(12) United States Patent
Irimia et al.

(10) Patent No.: US 8,043,846 B2
(45) Date of Patent: Oct. 25, 2011

(54) DEVICE AND METHOD FOR CONTACTING PICOLITER VOLUMES OF FLUID

(75) Inventors: Daniel Irimia, Charlestown, MA (US); Mehmet Toner, Wellesley, MA (US)

(73) Assignee: The General Hospital Corporation, Boston, MA (US)

( * ) Notice: Subject to any disclaimer, the term of this patent is extended or adjusted under 35 U.S.C. 154(b) by 1166 days.

(21) Appl. No.: 10/560,661

(22) PCT Filed: Jun. 9, 2004

(86) PCT No.: PCT/US2004/018370
§ 371 (c)(1),
(2), (4) Date: Oct. 31, 2006

(87) PCT Pub. No.: WO2005/010147
PCT Pub. Date: Feb. 3, 2005

(65) Prior Publication Data
US 2007/0099289 A1 May 3, 2007

(51) Int. Cl.
*C12M 1/34* (2006.01)
*B01L 3/00* (2006.01)
(52) U.S. Cl. ............... 435/288.5; 435/287.2; 422/82; 422/503; 422/130; 436/53; 366/DIG. 2; 366/DIG. 3
(58) Field of Classification Search .............. 422/82, 422/502, 503, 130; 436/53; 435/288.5; 366/DIG. 2, 366/DIG. 3
See application file for complete search history.

(56) References Cited

U.S. PATENT DOCUMENTS

| 6,130,098 | A | 10/2000 | Handique et al. |
| 6,150,119 | A | 11/2000 | Kopf-Sill et al. |
| 6,524,456 | B1 | 2/2003 | Ramsey et al. |
| 2002/0142471 | A1 | 10/2002 | Handique et al. |

FOREIGN PATENT DOCUMENTS

GB   2097692 A   * 11/1982

OTHER PUBLICATIONS

International Search Report mailed in International Application No. PCT/US04/18370 on Feb. 14, 2005.
Written Opinion mailed in International Application No. PCT/US04/18370 on Feb. 14, 2005.
International Preliminary Report on Patentability issued in International Application No. PCT/US04/18370 on Dec. 13, 2005.

* cited by examiner

*Primary Examiner* — William H Beisner
(74) *Attorney, Agent, or Firm* — Fish & Richardson P.C.

(57) ABSTRACT

The invention features devices for mixing fluids, e.g., for lysing cells, and methods of use thereof. One device is based on the ability to control the flow of fluids, e.g., by contact angle and channel size. Fluids in this device can be divided to form segments of controlled volume, which are then brought together to initiate mixing. An exemplary use of the device is for the lysis of single cells. Another device is based on the ability to two mix two fluids in a channel and affinity capture of analytes. The devices can be integrated on the same chip with other devices, for example, for cell handling or analysis of DNA, mRNA, and proteins released from the lysis of a cell.

17 Claims, 16 Drawing Sheets

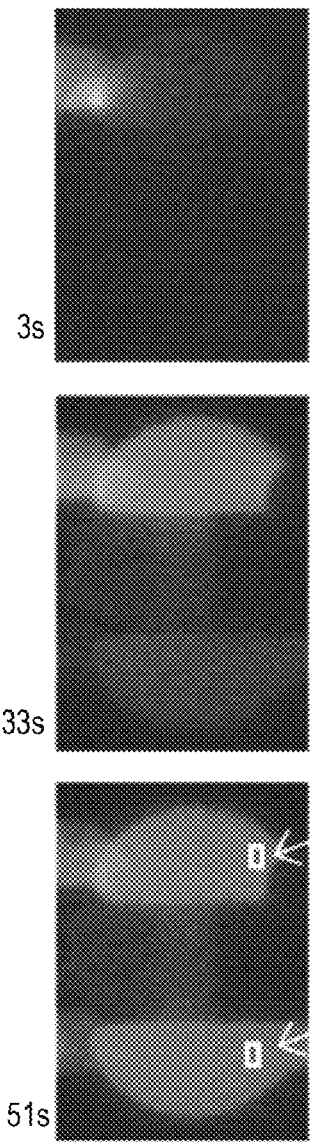
FIG. 7A
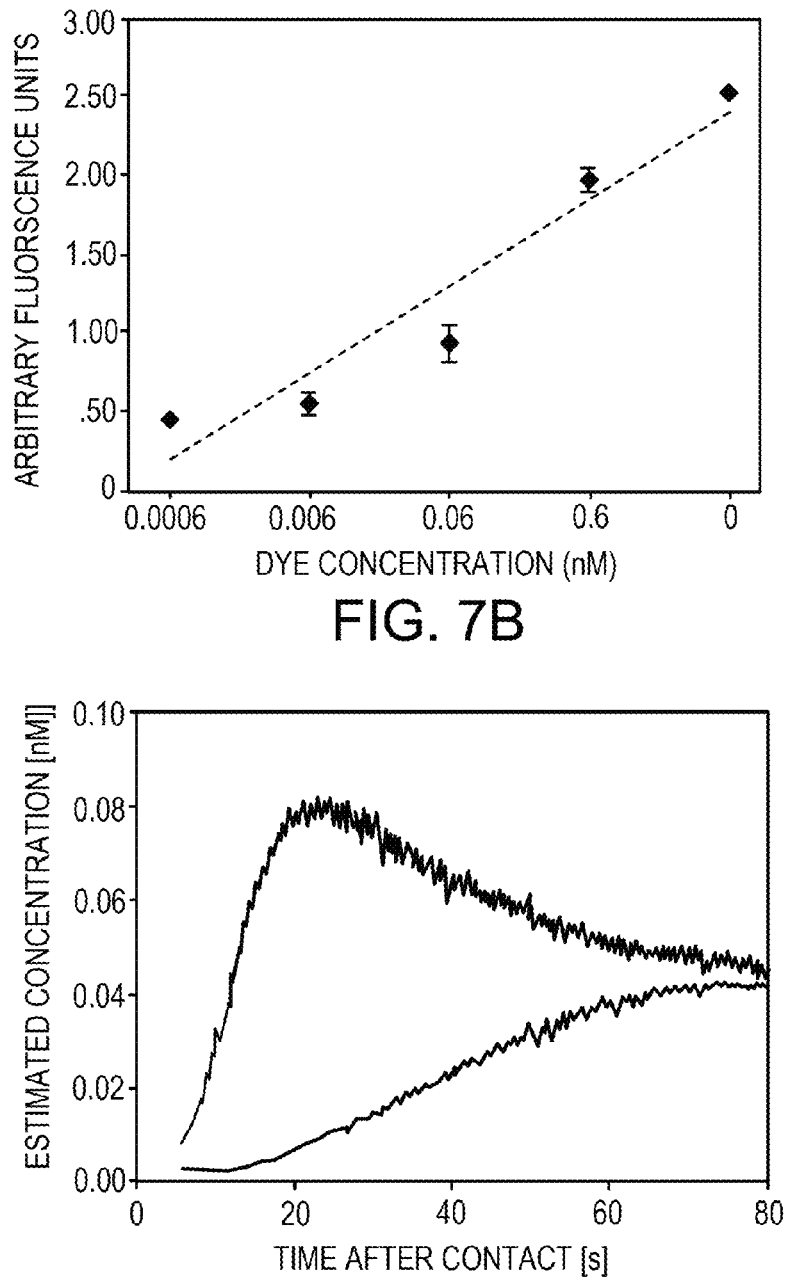
FIG. 7B
FIG. 7C

RNA gel electrophoresis. Tracks for 10ng control, RNA isolated from 677 and 1200 B lymphoblastoma cells using the microfabricated device.

DEVICE AND METHOD FOR CONTACTING PICOLITER VOLUMES OF FLUID

STATEMENT REGARDING FEDERALLY SPONSORED RESEARCH

This invention was made with Government support through the NIH (Grant 5 U54 GM62119-03). The Government has certain rights in this invention.

BACKGROUND OF THE INVENTION

The invention relates to the fields of microfluidics and cellular assays.

Better understanding of normal and pathogenic processes at the cellular level increasingly requires sensitive analysis of homogenous samples often containing only a few cells. One critical aspect of such analysis, considering the small amounts of target molecules contained in each cell, is to avoid excessive sample dilution and minimize losses. In addition, access to intracellular contents generally requires cell lysis, and current macroscopic approaches that work well on large samples cannot achieve controlled mixing of two solutions in volumes comparable to the cell volume. Cells are the basic structural and functional units of living organisms and analyzing the composition and behavior of individual cells is fundamental for understanding the physiology and pathology of any organism. Still, the majority of the biochemical methods employed in current biological research use samples containing several thousands of cells and as a result can only extract averaged information from the populations. Such global information is not always relevant to processes taking place in individual cells and concerted efforts are made to develop new techniques for quantitative analysis at single cell level.

In order to obtain comprehensive pictures of cell function, simultaneous examination of the expression of thousands of genes may be necessary. This examination is made possible by the development of microarray techniques for DNA and RNA. In general, simple knowledge of the gene sequence or the quantity of gene expression may be insufficient to predict biological functions or provide appropriate diagnostic information. Thus, several techniques to enable efficient and highly parallel identification, measurement, and analysis of proteins have been developed (e.g. protein-chip array).

Most array methods require concentrations of material above a certain threshold (e.g., 2 µg at 0.02 µg/µl concentration for MRNA analysis), and few methods can work with samples as small as 1000 cells. Flow cytometry can address issues of heterogeneity at the single cell level, but only for a small number of targets, which is limited by the number of fluorescent dyes available. In the case of genes, another limitation in the use of fluorescent probes comes from the requirement for a priori knowledge of the sequence of interest. Consequently, it has not yet been possible to address the issue of heterogeneity using current techniques for global analysis at the single cell level.

Previously reported techniques for single cell biochemical analysis involved the micropipette aspiration of the cell content, lysis of cells, and release of the molecules of interest in the surrounding environment form where they could be detected by capillary electrophoresis or electrochemical methods. Still, these methods cannot control the diffusion of the molecules into the surrounding medium and thus they are prone to errors when performing quantitative measurements. Some improvement may come from confining the diffusion to smaller volumes, e.g., by the use of microfluidic devices where intracellular contents from one or more cells have been released in a microchannel. In these systems, the progressively diminishing concentration of the molecule of interest due to the combined effects of diffusion and drift with time and distance from the source, complicate the attempts for quantification. Moreover, the reverse situation, where molecules from a fluid stream are slowly captured by one cell, locally decreasing their concentration, are difficult to probe and quantify under flow conditions. One way to address the sample dilution problem is by isolating cells in vials with volumes comparable to mammalian cell volume. Previously approaches used micro-vials, like the ones formed at the tip of micropipettes after etching. Problems with the control of fluid evaporation, and the lack of visual control of the cells in vials during experiments due to the geometry of the vial, limit the utility of such methods.

Thus, there is a need for new devices and methods for analyzing the contents of individual cells that have increased sensitivity.

SUMMARY OF THE INVENTION

The invention features devices for mixing fluids, e.g., for lysing cells, and methods of use thereof. One device is based on the ability to control the flow of fluids, e.g., by contact angle and channel size. Fluids in this device can be divided to form segments of controlled volume, which are then brought together to initiate mixing. An exemplary use of the device is for the lysis of single cells. Another device is based on the ability to two mix two fluids in a channel and affinity capture of analytes. The devices can be integrated on the same chip with other devices, for example, for cell handling or analysis of DNA, mRNA, and proteins released from the lysis of a cell.

In one aspect, the invention features a device for contacting two volumes of fluid. This device includes a first channel having a fluid inlet and a first fluid divider for dividing the fluid in the first channel into discrete segments; a second channel having a fluid inlet and a second fluid divider for dividing the fluid in the second channel into discrete segments; and a third channel connecting the first and second channels. The first or second fluid divider may include one or more sources for an immiscible fluid, such as an enclosed chamber connected to the first or second channel which may be heated, e.g., by a resistive heater or a radiation source. In one embodiment, a channel in the device may contain a constriction. The contact angle of an aqueous solution with the surface of the first, second, or third channel may be greater than 90°. The surfaces of the channel may also be modified, e.g., by light or an electric field, to have a contact angle of less than 90°. In another embodiment, the first or second channel includes a chamber having a volume of 0.1 pL–100 µL.

The device of the invention is used in a method of contacting two fluids including the steps of providing a device as described herein; pumping a first fluid through the inlet into the first channel and pumping a second fluid through the inlet into the second channel; employing the first fluid divider to divide the first fluid into a plurality of segments to form a first segment connected to the third channel; employing the second fluid divider to divide the second fluid into a plurality of segments to form a second segment connected to the third channel; and contacting the first and second segments via the third channel. In one embodiment, the first or second fluid divider, e.g., an enclosed chamber as described herein, includes one or more sources for fluid immiscible in the first or second fluid, and the immiscible fluid is introduced into the first or second channel to divide the fluid therein into a plurality of discrete segments. The contacting step may occur before, during, or after the fluid dividing steps. Segments of divided fluid have a volume, for example, of 0.1 pL-100 μL. Constrictions or sieves in the first or second channels may be employed to trap a particle, e.g., a cell, as fluid flows through the device. The contact step occurs, for example, by reducing the pressure in the third channel relative to the first and second channels or by reducing the contact angle of the first and second fluids with the third channel to less than 90°. In other embodiments, the first fluid has a contact angle of greater than 90° with the surfaces of the first and third channels, or the second fluid has a contact angle of greater than 90° with the surfaces of the second and third channels. An affinity capture agent may also be introduced into the device in the region where fluids are contacted. The affinity capture agent includes, for example, a bead, gel, or chemical species bound to the device surface.

Preferably, the first fluid includes a cell, and the second fluid includes a lysis solution capable of lysing the cell. In this embodiment, the first segment includes the cell, and the second segment includes the lysis solution, and the cell is lysed after the two segments are contacted.

The invention further features a method for capturing an analyte (e.g., a nucleic acid) including the steps of providing a device comprising a channel having a first and a second inlet and a region containing an affinity capture agent (e.g., silica or an ion exchange resin); introducing a first fluid into the channel via the first inlet; introducing a second fluid into the channel via the second inlet; allowing the first and second fluids to contact, wherein the contact results in the release or production of the analyte; and capturing at least a portion of the analyte on the affinity capture agent. The method may further include eluting the analyte from the affinity capture agent or removing the affinity capture agent from the device. The surfaces of the channel may also be derivatized to prevent adsorption of the analyte. In one embodiment, the first fluid includes a cell, and the second fluid is a lysing solution.

By "discrete" is meant physically separated.

By "fluid" is meant a liquid or gas. A fluid may be a solution or suspension, and it may carry particulate matter, e.g., cells.

By "immiscible" is meant does not substantially dissolve on the time-scale of operation of a device of the invention. An exemplary immiscible fluid for use with aqueous solutions is air.

By "lysis solution" is meant a solution that will cause at least one type of cell to lyse.

By "microfluidic" is meant having one or more dimensions of less than 1 mm.

By "θ" is meant the contact angle between a fluid and a surface.

The device of the invention has the capability of mixing two complex fluids, e.g., for lysing one or more mammalian cells in a closed chamber. The volume of the chamber is sized such that the final concentration of the cellular components in the lysis chamber is advantageously comparable to their concentration inside the cell. The device of the invention also has the following features and advantages: (1) the use of fluid expansion and fluid-fluid (e.g., liquid-gas) interface to separate volumes of fluid on the order of picoliters into discrete segments; (2) the use of constrictions or sieves to capture and position a cell from a cell suspension inside the device; (3) the use of fluid-fluid (e.g., liquid-gas) interfaces to control the flow path of a fluid in connecting channels; (4) the use of fluid expansion to manipulate the separated liquid volumes and achieve active mixing; (5) the use of electric currents, or other power sources such as radiation or chemical energy, to control the fluid volume separation and mixing on the chip, without the need for external pneumatic or mechanical actuators; (6) the use of magnetic beads inside the device for capturing and manipulation of specific molecules released during cell lysis; (7) the use of optically transparent materials to allow observation of the device by transmitted-light microscopy and similar techniques, simultaneously with cell manipulation and lysis; (8) the capability of integration with other microfluidic devices, both prior to introduction into (e.g., cell handling, incubation, or separation devices) and after introduction into (e.g., gene or protein microarray devices) the device of the invention; and (9) the capability of automation and massively parallel processing of individual samples (e.g., cells).

Other features and advantages will be apparent from the following description and the claims.

BRIEF DESCRIPTION OF THE DRAWINGS

FIG. 7A is a series of fluorescence images of the dye diffusing in the two compartments after the lysis of a single cell, and the dye concentration estimate. One cell loaded with fluorescent dye was captured in the 25 pL upper chamber and lysed by 25 pL of GTC lysing solution, releasing the intracellular fluorescent dye into the 50 pL total volume. The fluorescent dye diffused very fast into the cell lysis chamber and then slowly through the mixing channel and into the lower chamber. Pictures were taken at 3, 33, and 51 seconds after the contact between cell suspension and lysing solution. Arrows and boxes indicate the fields where the fluorescence intensity was measured.

FIG. 7B is a calibration curve generated by measuring the fluorescent signal from solutions of known concentration of dye.

FIG. 7C is a graph of the concentrations of the released fluorescent dye in the upper (dotted line) and lower (solid line) chambers calculated from the fluorescence signal using the calibration curve. The concentration in the upper chamber reached a peak at 20 seconds after the lysis started. Steady state was achieved after approximately 90 seconds.

DETAILED DESCRIPTION OF THE INVENTION

Figure 1:
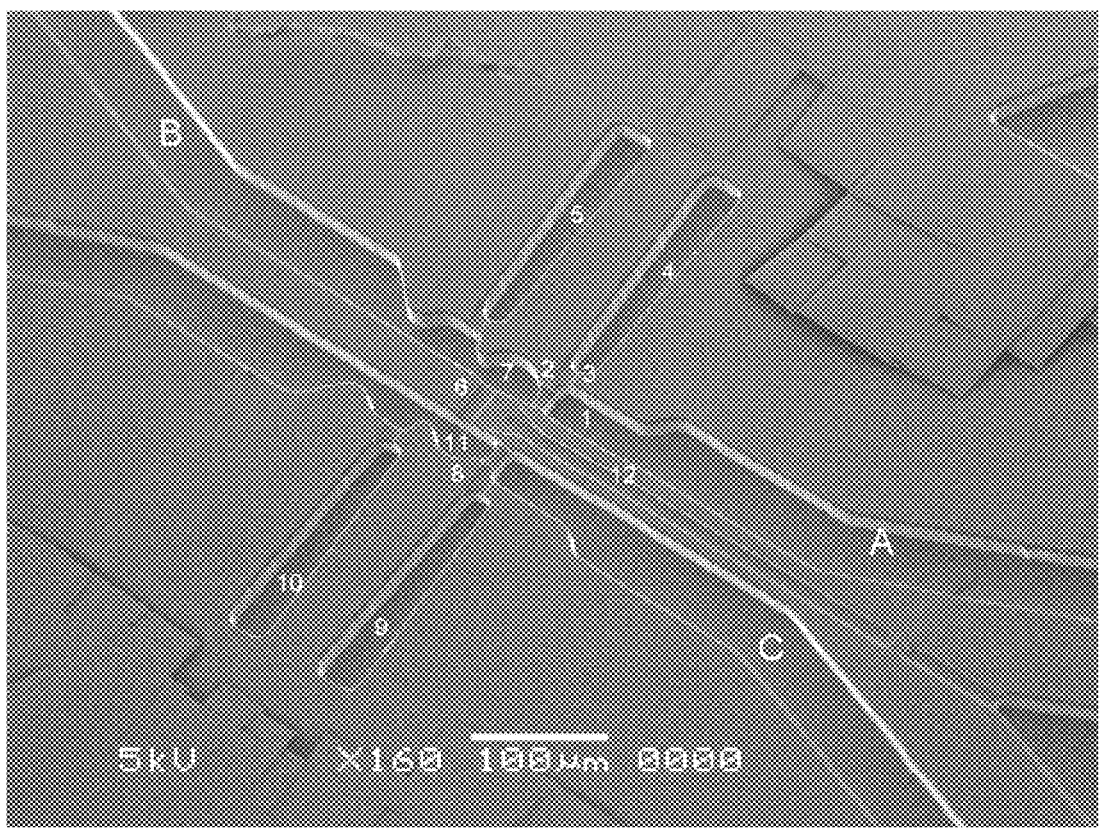
FIG. 1 is an electron micrograph of a lysis device of the invention. Letters and numbers correspond to different sections of the channels as described below.

The invention features devices and methods for contacting two or more volumes of fluid. In one example, the device of the invention is capable of capturing a single cell and lysing it in an isolated chamber with a total volume (~50-100 pL) comparable to or within several orders of magnitude of the cell volume (~2 pL). In this embodiment, the molecules released by lysis are present in concentrations similar to intracellular concentrations. In other embodiments, other fluids containing, for example, samples, reagents, or synthetic precursors, may be contacted using the device and methods of the invention. In another device, two or more fluids are contacted in a microchannel and products of that contact (e.g., cellular lysate) are captured on affinity agents.

Devices of the invention may be used as one component of an analytical device. Products produced by the interaction of two fluids or material bound to an affinity capture agent may be transported, on-chip or through other means, for additional analysis, collection, reaction, or disposal. For example, devices of the invention may be integrated up or downstream with other microdevices for automated expression profiling (e.g., via microarray technology) from small cell populations and cell separation devices. The ability to integrated with other devices would allow the preliminary purification of raw samples (e.g., whole blood) prior to manipulation of a desired component (e.g., monocyte). Downstream processing may also require further purification or manipulation once a sample is prepared using the devices of the invention.

Picoliter Mixing Device

The device typically contains two main channels connected by a third, connecting channel. Although some fluid from the main channels may enter the connecting channel, that fluid does not come into contact via the connecting channel without appropriate actuation. For example, when using aqueous solutions and hydrophobic channels, entry of fluid into the connecting channel is typically minimized by reducing the cross-sectional area of that channel relative to the main channels. In general, the surfaces of the main channels and connecting channels are designed such that the fluids being added to the channels maintain a contact angle ($\theta$) of greater than 90°, such that fluids do not wet the channels by capillary action, thereby ensuring that additional pressure is needed to push fluid into those channels. Valves may also be used to control the entry of fluid into various channels or chambers. Channels in the device may have any cross-section capable of passing the fluids of interest, e.g., circular ot rectangular. The surfaces of the channels may be hydrophobic or hydrophilic depending on the nature of the fluid introduced into the main channels. The main channels may also include enlarged areas to form chambers of defined volume for mixing.

The device also includes fluid dividers for dividing the fluid in the main channels into segments by introducing a fluid into the main channels. This introduced fluid is preferably immiscible in the fluid in the main channels. The main channels may also contain constrictions to prevent fluid flow beyond a defined point, e.g., to minimize the usage of reagents or to trap particulate matter. Constrictions or sieves (e.g., a series of posts) can also be employed to trap particles in the device.

Fluid dividers may be any device that is capable of dividing a column of fluid into segments, for example, by introducing an immiscible fluid into the fluid columns in the main channels. Typically each main channel has two fluid dividers to divide the fluid in the main channel into three segments, thereby isolating the middle segment. Additional fluid dividers may be present to divide the fluid in the main channels into more than three segments, e.g., for parallel or serial processing of multiple volumes of fluid. Examples of fluid dividers include pumps that force fluid (e.g., air or a hydrocarbon) into the main channels. One exemplary fluid divider includes an enclosed chamber of fluid that has an inlet into the main channel. When heated, e.g., by a radiation source such as a laser or a resistive heating element, fluid in the chamber expands and flows into the main channel. Preferably, the channels have a round cross-section when employing fluid dividers that introduce fluids, but other cross-sections, e.g., rectangular, may also be employed. Alternatively, a fluid divider may be a series of mechanical valves that physically divide a fluid column into segments when closed. In this case, the channel containing the segment of fluid to be manipulated further in the device preferably has an inlet (e.g., a small channel or a valve) for a fluid, e.g., air, to equalize the pressure as the fluid segment is transported in the device. In another embodiment, the fluid divider may be a heater capable of nucleating a gas bubble in the fluid column, or the divider may involve a chemical or electrochemical reaction capable of evolving gas. The amount of immiscible fluid introduced or generated into the channels by the dividers will depend on the volume of the channels in the device. Combinations of various fluid dividers may also be employed in a single device.

The device may allow for the pressure in the connecting channel to be reduced relative to the pressure in the main channels in order to cause fluids in the main channels to come into contact. This effect may occur, for example, by applying reduced pressure (e.g., suction) to the connecting channel or by increasing the pressure in the main channels. Alternatively, the $\theta$ of the fluid in the main channels with the connecting channel may be altered to cause fluids in the main channels to come into contact by application of light or an electric field to the connecting channel or introduction of additives to the fluid. The connecting channel may also be connected to an outlet channel for applying suction, removing the products of the fluids contacted in the device, and providing active mixing.

An exemplary device of the invention is shown in FIG. 1. The device includes two main channels having three inlets for fluids, A, B, and C. Both of the main channels include a constriction (labeled 2 in the A/B channel and 8 in the C channel). Fluid introduced via the A or B inlet may be pumped into the channel until reaching constriction 2. The constriction in the channel may prevent the passage of particulate matter. A third channel 6 connects the two main channels and is, in turn, connected to a channel 12 through which suction may be applied and the contents of channel 6 removed. Each of the main channels contains a chamber (labeled 7 in the A/B channel and 11 in the C channel) that houses the volume of fluid to be contacted via channel 6. The fluid dividers are chambers 4, 5, 9, and 10, two of which flank each chamber 7 and 11. Each of chambers 4, 5, 9, and 10 contains a heater. The dimensions of the channels in the device are typically microfluidic.

In another embodiment, each main channel includes only one fluid divider, which divides the fluid column into two segments. The device may be designed such that each main channel has a constriction through which the introduced fluid cannot flow. The location of the fluid divider relative to the constriction then determines the volume of the fluid segment separated from the remainder of the fluid column.

In an alternative embodiment, the fluids to be mixed in the device have a $\theta$ of less than 90° with the surfaces of the main channels, such that the fluids wet the main channels by capillary action. The surfaces of channels connecting the main channels have a $\theta$ greater than 90°, thereby preventing the contact of the fluids in the main channel until the relative pressure of the connecting channel is reduced. In this embodiment, enclosed fluid chambers, e.g., as depicted in FIG. 1, may be used as the fluid divider. The $\theta$ of the surfaces of the enclosed chambers may also be greater than 90° in order to prevent entry of fluids from the main channels. Alternatively, the $\theta$ surfaces of the enclosed chamber may be less than 90° if the fluid in the enclosed chambers cannot be substantially displaced by the fluid in the main channels.

In another embodiment, the contacting of fluids in the connecting channels can be controlled by the length of the connecting channel. For example, fluids are introduced into the main channels and begin to flow into the connecting channel. The fluid dividers can then be operated to divide the fluid columns in the main channels. This division may occur before the fluids contact in the connecting channel, as the fluids are contacted, or shortly after the fluids contact. The length of the connecting channel can be adjusted to control the time of contact relative to the actuation of the fluid dividers.

A device of the invention may also include more than two main channels, from which fluids may be contacted. For example, fluids from three or more channels may be contacted simultaneously or in series. In addition, the device may be designed to allow parallel or sequential contacting of fluids from fewer than all of the main channels. Such an arrangement may be two-dimensional or three-dimensional. In addition, fluid introduced into the main channels of the device may be the output from another device, e.g., a cell separator or chromatograph. The fluid produced on the device may also be directed into another device, e.g., a capillary electrophoresis chip, for further manipulation. Such additional devices may be integrated onto the same chip as the device of the invention, or the additional devices may be physically separated.

Operation of Picoliter Mixing Device

A device of the invention may be employed for any purpose requiring the contacting of two fluids, e.g., synthesis of species (e.g., in situ synthesis of sensitive, highly reactive, or hazardous reagents), assays (e.g., biochemical or cellular assays), labeling of species (e.g., proteins or cells), and destruction of species (e.g., lysis of cells or degradation of macromolecules). The devices may be employed in a variety of fields, such as medical diagnostics, environmental or quality control monitoring, and basic research. An exemplary use of the device of the invention is the lysis of one or more cells for biochemical analysis of the lysate. A device of the invention may be controlled using electric currents, and no supplementary devices outside the chip are necessary. Thus, the automation of the use of devices of the invention is highly feasable.

In general, the device is operated by filling each main channel, dividing the fluid columns in one or more of the main channels, and causing segments of fluid to come into contact via a channel connecting two or more main channels. Constrictions or sieves in the channels may be used to trap particles, e.g., cells, in the segments that are to be contacted. Such trapping may occur by flowing a liquid sample into the channel until a particle reaches the constriction, or once a particle is introduced into a channel, gravity could be used to move the particle to the constriction, Particle capture may also be achieved by other methods, such as dielectrophoretic trapping, capture using antibodies or other binding molecules fixed to surfaces or structures in the device, and polymer brushes. In one embodiment, the segments are forced into contact by reducing the pressure in the connecting channel relative to the main channels, e.g., by applying suction to the connecting channel. In another embodiment, the surface of the connecting channel can be altered to reduce the $\theta$ of the fluid to below 90°, and fluid will spontaneously flow into the connecting channel. Alternatively, an additive may be introduced into the fluid in order to lower $\theta$, e.g., introducing a surfactant into an aqueous solution. The volumes contacted can range from 0.1 pL to 100 µL, typically in the picoliter range. Once contacted, fluids may then mix actively or passively. In one embodiment, active mixing is achieved by drawing fluid in the connecting channel into another channel and then forcing the fluid back into the third channel. This process may be repeated until a desired level of mixing is achieved. For example, the connecting channel may be in communication with a chamber. This chamber is normally heated and is far enough from the connecting channel or insulated such that a normal temperature is still maintained in the connecting channel. After the fluid division and contact, the heated chamber is allowed to cool. The pressure inside the chamber will reduce, and fluid will be pulled from the connecting channel towards the chamber. By reheating the chamber, fluid is pushed back into the connecting channel. The magnitude, frequency and rate of this back and forth movement of fluid can be controlled, e.g., by the current applied to a resistive heater in the chamber. Alternatively, the connecting channel is in communication with a syringe or any other device that can achieve a controlled change in pressure over the time scale of interest.

After contact, the contents of the mixture of the two fluids may be collected for further reaction, separation, storage, or analysis. Products formed or released by the contacting of fluids on the device may be bound by particles (e.g., magnetic or non-magnetic beads that contain specific or non-specific binding groups) in one or both of the fluids mixed. If a device having constrictions through which beads cannot pass is employed, beads may be rinsed in the device by passing buffer through the channels. Alternatively, the products may be removed as a fluid or analyzed on the device.

In one embodiment, the fluids to be mixed have a θ with the channel surfaces of greater than 90°. The pressure needed to move such a fluid through a channel increases as the cross-sectional area of the channel decreases. The pressure necessary for pumping can be calculated using the surface tension of the fluid ($\sigma$), the contact angle ($\theta$) as defined before, and the radius of curvature (r) inside the channel into which fluid is pumped ($P=2\times\sigma \cos(\theta)/r$). As a consequence, the movement of the fluid in a device can be controlled by controlling the pressure applied to the fluid and the cross-sectional area of the channels. Using an appropriate combination of θ, cross-sectional area, and pressure, fluids may be pressure pumped into a channel without substantially entering a connected channel. In addition, the introduction of constrictions in a channel can be used to prevent the passage of fluid beyond a defined point.

When fluids have been introduced into the main channels, a fluid divider may be employed to segment the fluid column in one or more main channels. The actuation of the fluid divider will depend on its nature. For example, for fluid dividers that require heat to cause fluid expansion into the main channel or bubble nucleation, a voltage is typically applied to a resistive heating element. A radiation source, such as a laser, may also be used as a heat source. Alternatively, a chemical reaction may be used to generate heat or evolve gas. For a fluid divider including a heater in an enclosed chamber, fluid in the main channels may remain divided even after cooling because of the hystersis in the advancing and receding θ. If the fluid divider introduces a fluid into the fluid column of the main channel, the fluids in the main channels are preferably saturated in the fluid used to divide them. The channel may be designed to direct the flow of the imiscible fluid in the channels. For example, constrictions in the main channels may be used to prevent or reduce immiscible fluid flow in a particular direction. For other fluid dividers, e.g., such a mechanical valves, the divider may be actuated mechanically, electrically, magnetically, or chemically in order to close the valves.

The devices of the invention may be employed in an array format, i.e., the presence of many individual devices in a larger structure. Employing a laser heating system, as described above, would allow for individual actuation of fluid dividers without the need for multiple electrical connections.

Fluids to be mixed in the device are preferably aqueous, but organic liquids or even gases may also be employed. When gases are employed, the device is filled with a liquid prior to introduction of the gases to prevent expansion of the gas through the device.

Figure 11:
FIGS. 11A and 11b are micrographs showing the use of beads in a device of the invention.
Figure 11:

Affinity capture agents, e.g., beads, may be present in the device. For example, affinity capture agents are introduced into the device in one or both of the fluids to be mixed, are immobilized in the device in the regions where mixing takes place (e.g., adsorbed or chemically bound to the surfaces of the channels or part of a gel or other matrix), or are introduced into the mixing region independently of the fluids being mixed. Affinity capture agents may be used to bind analytes of interest released when the fluids are mixed, e.g., intracellular contents or reaction products. Such analytes may be bound specifically (e.g., by specific antibodies, ligands, receptors, or complementary nucleic acids) or non-specifically by the affinity capture agent (e.g., by electrostatic, hydrophobic, or hydrophilic interactions). Appropriate affinity capture agents for various analytes are known in the art. Exemplary agents include gels and beads (e.g., magnetic beads). Suitable materials include polystyrene, silica, alumina, ion exchange resins (anionic or cationic), and poly-dT magnetic beads. Anion exchange resins capture negatively charged molecules that can be subsequently eluted in high-salt solutions. Silica gel captures molecules in high-salt solutions; and the molecules are released in low-salt solutions. Poly-dT beads specifically capture mRNA. FIG. 11 illustrates the use of beads in a lysis device as described herein.

Continuous Flow Mixing Device and Operation

A continuous flow mixing device of the invention typically contains one main channel into which a plurality of fluids may be introduced. The device may be used to extract analytes, e.g., high quality nucleic acids, that may be used for microarray protocols from samples, e.g., those containing small numbers of cells.

Figure 12:
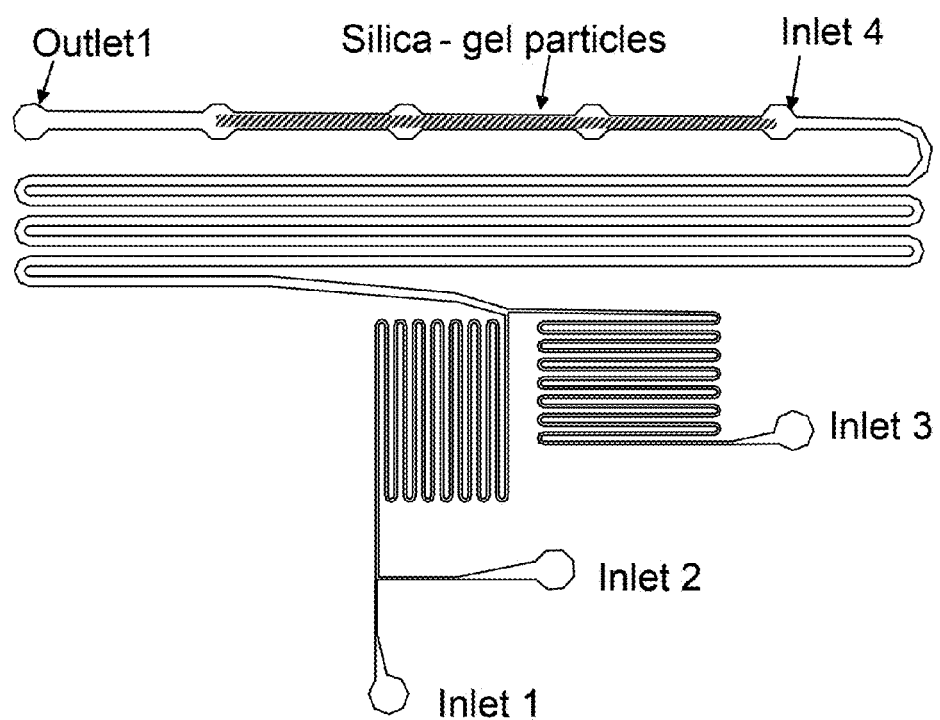
FIG. 12 is a schematic diagram of a device for continuous flow mixing and analyte capture.

In one embodiment, the microfabricated device contains a network of channels of different sizes connecting to four inlets and one outlet (FIG. 12). Samples, e.g., containing cells, are introduced through inlet 1. A second solution, e.g., lysing solution, is similarly introduced through inlet 2, and a third solution, e.g., ethanol, may be introduced through inlet 3. Inlet 4 may be used to introduce affinity capture agents, e.g., silica-gel particles or anion exchange resin beads, in the terminal section of the channel, and also to introduce eluant to elute analytes from the affinity capture agent at the end of the assay. Inlet 4 is typically sealed after the introduction of the affinity capture agent. Alternatively, other affinity capture agents including gels or species bounds to the channel surfaces may be used as described for the picoliter mixing device. Outlet 1 may be connected to a micropump drawing liquid from the channel, e.g., at a rate of 1 to 20 μL/min, such as 5 to 10 μL/min.

Once the two or more fluids are contacted in the device, the products are passed through the channel to the affinity capture agent where specific or non-specific binding occurs. Fluids may be contacted in various ratios, e.g., from 1:2 to 1:5. The ratio may be controlled by differences in the cross-sectional area of the channels or by varied flow rates through two or more inlets. Once binding has occurred, the channel is then typically rinsed, and any analyte captured on the affinity capture agent can be eluted using an appropriate eluant or the capture agent may be removed from the device. The volume of eluant employed, e.g., 5 to 50 μL, may be chosen to the maximum concentration of eluted analyte. The analyte may then be isolated or subjected to additional analyses.

Although typically operated in a continuous flow regime. Fluid flow may be arrested during the assay, e.g., to provide additional time for mixing, lysis, or reaction. Flow can be stopped by clamping the inlets or the outlet using macroscopic clamps or valves inside the device. One application of arresting flow is the enzymatic digestion of proteins in the sample (e.g. the use of proteinase K for the digestion of RNases in the sample).

Fabrication

A variety of techniques can be employed to fabricate a device of the invention, and the technique employed will be selected based in part on the material of choice. Exemplary materials for fabricating the devices of the invention include glass, quartz, silicon, steel, nickel, poly(methylmethacrylate) (PMMA), polycarbonate, polystyrene, polyethylene, polyolefins, epoxy resins, poly(ethylene glycol), silicones (e.g., poly(dimethylsiloxane) (PDMS)), and combinations thereof. Other materials are known in the art. In one embodiment, the device is fabricated, at least in part, from a transparent material to allow for visual inspection or optical measurements (e.g., fluorescence or absorbance).

Methods for fabricating channels in these materials are also known in the art. These methods include, photolithography (e.g., stereolithography or x-ray photolithography), molding, casting, embossing, silicon micromachining, wet or dry chemical etching (e.g., reactive ion etching or deep reactive ion etching), milling, diamond cutting, Litbographie Galvanoformung and Abformung (LIGA), and electroplating. For example, for glass, traditional fabrication techniques of photolithography followed by wet (KOH) or dry etching (reactive ion etching with fluorine or other reactive gas) can be employed. Techniques such as laser micromachining can be adopted for plastic materials with high photon absorption efficiency. This technique is suitable for lower throughput fabrication because of the serial nature of the process. For mass-produced plastic devices, thermoplastic injection molding, and compression molding is suitable. Conventional thermoplastic injection molding used for mass-fabrication of compact discs (which preserves fidelity of features in submicrons) may also be employed to fabricate the devices of the invention. For example, the device features are replicated on a glass master by conventional photolithography. The glass master is electroformed to yield a tough, thermal shock resistant, thermally conductive, hard mold. This mold serves as the master template for injection molding or compression molding the features into a plastic device. Depending on the plastic material used to fabricate the devices and the requirements on optical quality and throughput of the finished product, compression molding or injection molding may be chosen as the method of manufacture. Compression molding (also called hot embossing or relief imprinting) has the advantages of being compatible with high-molecular weight polymers, which are excellent for small structures, but is difficult to use in replicating high aspect ratio structures and has longer cycle times. Injection molding works well for high-aspect ratio structures but is most suitable for low molecular weight polymers.

A device may be fabricated in one or more pieces that are then assembled. Layers of a device may be bonded together by clamps, adhesives, heat, anodic bonding, or reactions between surface groups (e.g., wafer bonding). Alternatively, a device with channels in more than one plane may be fabricated as a single piece, e.g., using stereolithography, multi-layer fabrication techniques, or other three-dimensional fabrication techniques.

In one embodiment, the device is made of PMMA. The features, for example those shown in FIG. 1, are transferred onto an electroformed mold using standard photolithography followed by electroplating. The mold is used to hot emboss the features into the PMMA at a temperature near its glass transition temperature (105° C.) under pressure (5 to 20 tons) (pressure and temperature will be adjusted to account for high-fidelity replication of the deepest feature in the device). The mold is then cooled to enable removal of the PMMA device. A second piece used to seal the device, composed of similar or dissimilar material, may be bonded onto the first piece using vacuum-assisted thermal bonding. The vacuum prevents formation of air-gaps in the bonding regions.

In addition to channels, other components, such as heaters, valves, and sensors (e.g., to detect specific conditions or components of the products of the device, such as pH, conductivity, or specific ions), may be fabricated in the device. Techniques are known in the art for the fabrication of such components. For heaters, resistive elements (e.g., metal or ceramic strips) may be molded into a device or evaporated or otherwise deposited onto the device. When a voltage is applied, the resistive element emits heat. Connections to external fluid sources or receptacles may be made by any standard means, e.g., Luer locks, compression fittings, and threaded fittings.

Chemical Derivitization

The surfaces of the device may be treated in order to ensure that the $\theta$ is greater (or lesser) than 90°. Alternatively, the device may be fabricated out of a material that provides the appropriate $\theta$. Surface coatings whose $\theta$ may be changed, e.g., by the application of light or an electric field, may also be employed. Examples of such coatings include titanium oxide and polypyrrole. To reduce non-specific adsorption of cells or compounds introduced, released, or formed during operation of the device onto the channel walls, one or more channel walls may also be chemically modified to be non-adherent or repulsive, such as a thin film coating (e.g., a monolayer) of commercial non-stick reagents, such as those used to form hydrogels. Additional examples of chemical species that may be used to modify the surfaces of a device include oligoethylene glycols, fluorinated polymers, organosilanes (e.g., $C_{12}H_8F_{17}SiCl_3$), thiols, poly-ethylene glycol (e.g., having a molecular weight of 1000 to 20,000), poly-ethylene glycol gels, poly-vinyl alcohol, mucin, poly-HEMA, methacrylated PEG, and agarose. Charged polymers may also be employed to repel or attract oppositely charged species. Pretreatment of the channels with blocking agents such as tRNA and BSA may also be used to reduce non-specific adsorption. Surfaces of the device may also be treated in order to capture materials produced or released in the device, e.g., small molecules, membrane fragments, or proteins. Mixtures of surface coatings may also be employed, e.g., a hydrophobic coating and a coating capable of binding specific molecules, as long as the $\theta$ is maintained at an appropriate value, e.g., greater than 90°. The type of chemical species used for surface modification and the method of attachment will depend on the nature of the fluid in the channel, the nature of the walls, and the species being attached. Surface coatings may be covalently or non-covalently attached. Such surface modification techniques are well known in the art. The surfaces of the device may be functionalized before or after the device is assembled.

The following examples are intended to illustrates various features of the invention are not intended to be limiting in any way.

EXAMPLE 1

Fabrication of a Picoliter Mixing Device of the Invention

A device of the invention was microfabricated using standard techniques. Channels were patterned in PDMS by casting the polymer on a mold of SU-8 photoresist photopatterned on glass. Three different layers of SU-8 were patterned on the same substrate in order to create structures with different heights that correspond to channels of different cross sectional dimensions in the PDMS slab. Micro-heaters were fabricated by patterning gold electrodes on glass. The PDMS slab and the glass with the electrodes were aligned and bonded using oxygen plasma. The surfaces of the channels (both the PDMS and the glass) were modified using fluorosilane and rendered hydrophobic. The assembled device contains a series of channels with different widths and heights as shown in FIG. 1, and in more detail in FIG. 2.

The dimensions of the device were as follows: channel 1: 30×85×15 µm (w×l×h); constrictions 2 and 8: 12.5×12.5×4 µm; channel 3: 12.5×15×2 µm; chambers 4, 5, 9, and 10: 22 to 38×200×15 µm; channel 6: 12.5×38×3 µm; channel 12: 12.5×450×4 µm; chambers 7 and 11: semicircles with radius 30 µm and 15 µm high; and the triangular region between channel 6 and channel 12 was 2 µm high.

EXAMPLE 2

Lysis of a Cell Using a Picoliter Mixing Device of the Invention

Figure 2:
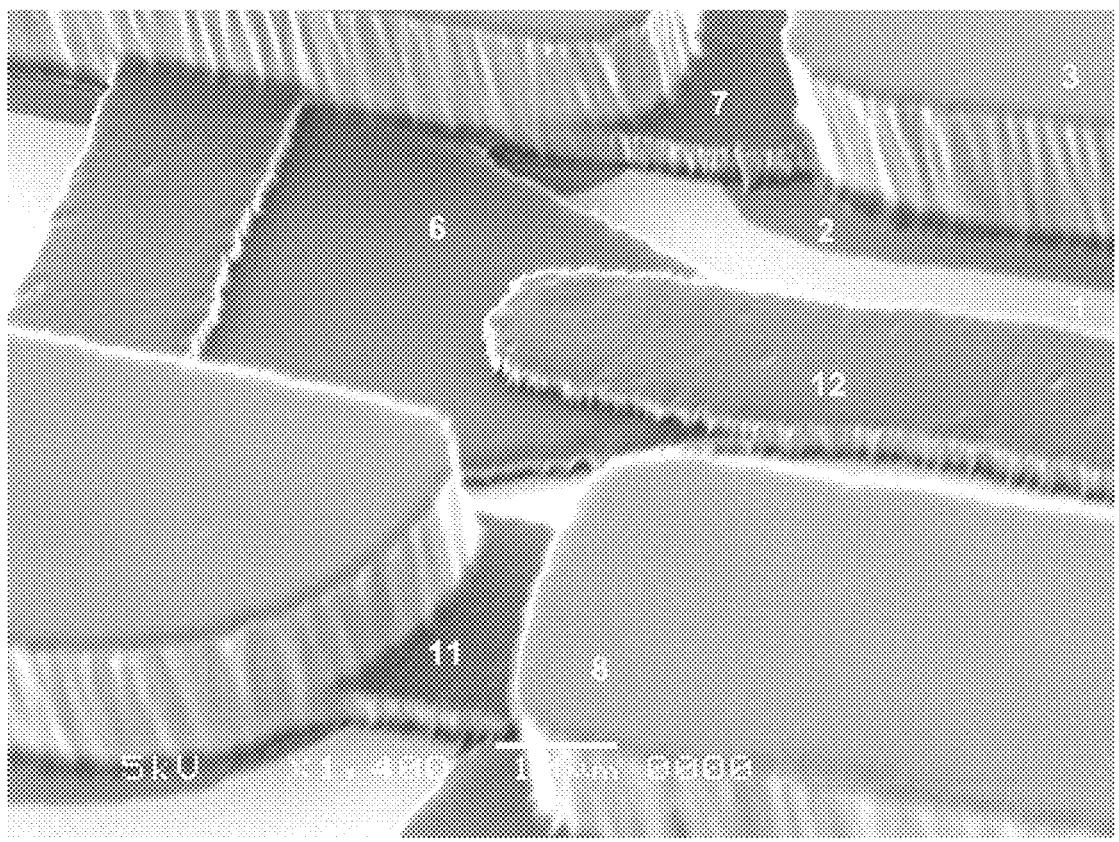
FIG. 2 is an electron micrograph of the lysing chambers and adjacent channels of the device shown in FIG. 1. Cells are trapped and separated in chamber 7 while a volume of the lysing solution is separated in chamber 11. The fluids in chambers 7 and 11 are mixed by suction in channel 6. The contents of the chambers 7 and 11 and channel 6 can be removed through channel 12.

Referring to FIGS. 1 and 2, an isotonic phosphate buffer solution (PBS) was introduced through inlet A. By applying moderate pressure (~20 kPa), the PBS was pushed through channel 1, and the fluid was stopped at constriction 2. The fluid also did not enter channel 3, and, as a consequence, air was trapped in chamber 4. A cell suspension of 3T3 mouse fibroblast or MOLT-T lymphoblasts was introduced through inlet B. The liquid column joined the PBS column while air was trapped in chamber 5. The liquid would not pass through channel 6 unless too high a pressure was applied (~80 kPa). While fluid could flow through constriction 2, cells larger than the constriction were trapped in chamber 7. Similarly, the lysing solution (3 M guanidine thiocyanate in water) was introduced through inlet C and pushed through constriction 8, trapping air in chambers 9 and 10. When the desired number of cells (one or more) was trapped in chamber 7, a pulse of current of controlled duration and intensity was applied to the heaters, and the air trapped in channels 3, 5, 9 and 10 expanded into the nearby channels, separating the fluid columns into three segments each. A cell was trapped in the middle segment, corresponding to chamber 7, still separated from the lysing solution separated in chamber 11 (FIG. 2). When suction is applied through channel 12, fluid from both chambers 7 and 11 is pulled into channel 6, and the two liquids contacted and were mixed by diffusion. This contact lead to the release of the cell contents in the isolated space of chambers 7 and 11 and channel 6. Beads may be introduced simultaneously with the cells, and specific components of the cell can be captured on the surface of the beads and kept in place during subsequent washing steps. The content of the lysing chambers could also be removed through channel 12 and taken out of the device or moved into a different section of the device for further analysis.

EXAMPLE 3

Exemplary Picoliter Mixing Device

In one exemplary device, cells and fluids are independently isolated in two microchambers having 25 pL volumes, through the coordinated action of four on-chip thermopneumatic actuators and using the hysteresis in the liquid-solid contact angles. The two volumes are initially separated by virtual walls formed by liquid-air interfaces in the hydrophobic capillary connecting the two microchambers, and then mixed by drawing the air out of the capillary. The use of the microfabricated device is exemplified on two assays at the single cell level, one for estimating intracellular concentration of a preloaded fluorescent dye, and one for evaluating intracellular amount of insoluble, filamentous actin.

Principles of Device Design. Precise manipulation of liquids, air, and cells inside the device is achieved through passive and active control structures. As shown in the schematics in FIGS. 3A-3D, the device consists of a network of hydrophobic channels and chambers of different sizes, symmetrical by the longitudinal axis. The main channels have 50 µm width and 20 µm depth for most of their length, but narrow down to 30×20 µm, then to 15×20 µm in the vicinity of the cell lysis chamber. Smaller channels, 12.5 µm wide and 3 to 51 µm deep, communicate between the air chambers and the main channels and act as passive valves, restricting the liquid flow and trapping air inside. Within the main channel, the narrowest tapering forms a 15×5 µm weir that allows fluid to move through, but is not large enough for cells to pass, entrapping them inside the lysis chamber (FIG. 3A). In combination with the mentioned passive control structures, four thermopneumatic actuators are used to separate 25 pL volumes of fluids in each of the two lysis chambers (FIG. 3C). A 12.5×5 µm mixing channel connects the upper and lower sections of the lysis chambers and another 12.5×5 µm sampling channel is used to evacuate the air from the mixing channel, bringing the liquids in the two sections of the lysis chambers into contact and allowing them to mix, and leading to cell lysis (FIG. 3D). The implementation of the microfluidic network and the electric heaters, into a functional device employed the assembly of an elastomeric block with patterned channels of different cross-sectional area onto a glass slide with thin film electric heaters, and is outlined below.

Figure 3:
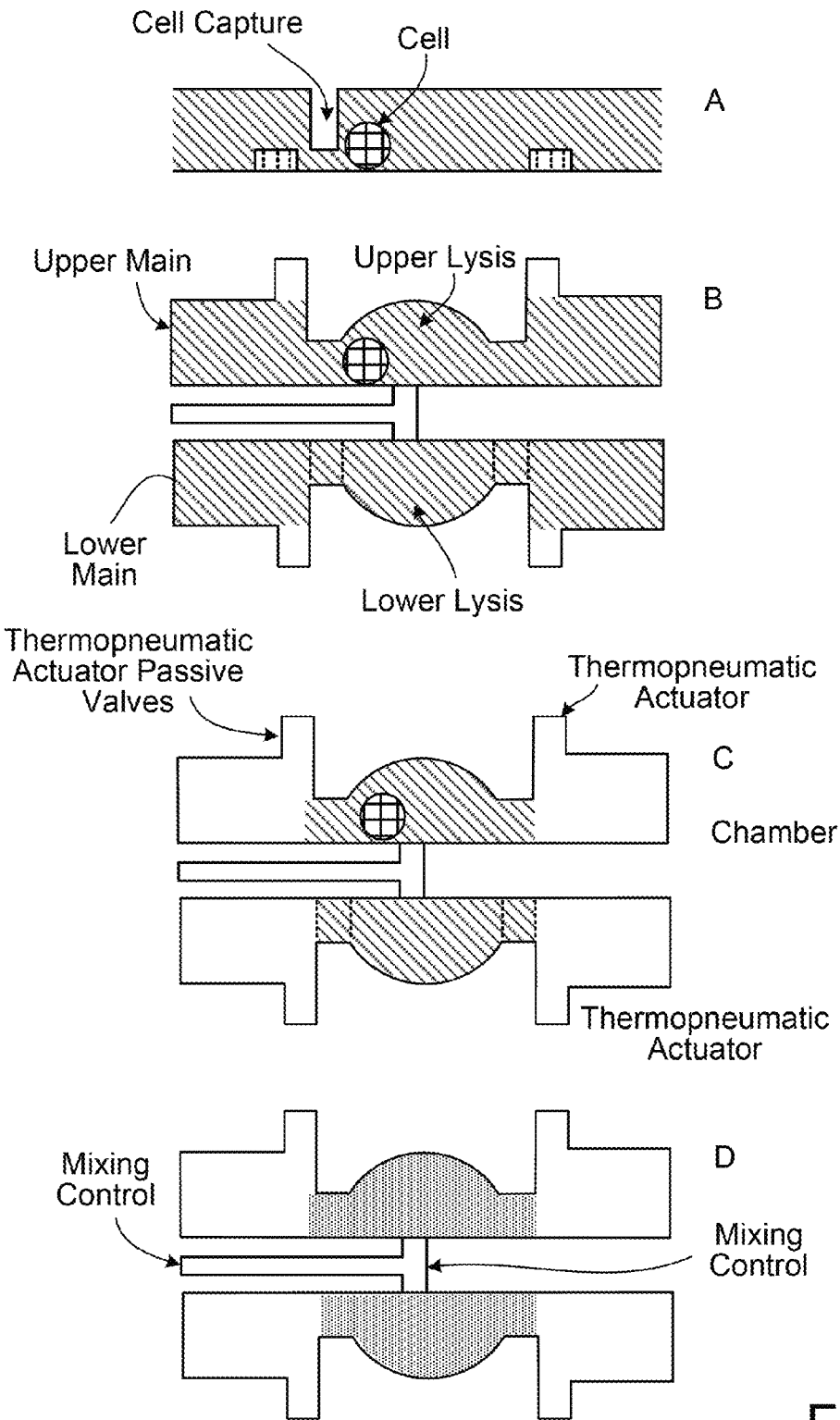
FIGS. 3A-3D are schematic diagrams of device functioning steps. A. One cell was introduced with the fluid in the upper main channel and captured in the cell lysis chamber by the use of a dam like structure. B. Lysing solution was introduced into the lower main channel. C. Fluid compartments were formed in each of the chambers by the coordinated action of four thermopneumatic actuators. D. Cell lysis was achieved by the contact and mixing of the fluids in the two chambers.

Photoresist Mold. Structures of 3, 5 and 20 µm thicknesses, complementary to channels of corresponding depths, were fabricated using three layers of SU8 epoxy based photoresist (Microlitography Corp. Newton, Mass.) on the same wafer. Glass slides (45×50×0.1 mm, Fisher, Pittsburgh, Pa.) were thoroughly cleaned using a 3:1 volumetric mixture of sulfuric acid (Ashland Chemical, Columbus, Ohio) and hydrogen peroxide (Ashland Chemical), and then exposed to oxygen plasma in a parallel plate plasma asher (March mc, Concord, Calif.). A thin film of chrome (50Å) was sputtered on the glass coverslips (Goodard and Asoc, Foster City, Calif.) and then patterned to form alignment marks for the subsequent fabrication steps. For this purpose, the glass slides were coated with a 1 µm thin layer of negative photoresist (AZ1512, Clariant, Somerville, N.J.) using a spin coater (Solitec Wafer Processing, Inc., Milpitas, Calif.), and the photoresist was patterned by exposure to ultraviolet light (15mW/cm$^2$) in a mask aligner (Quintel Co., San Jose, Calif.) for 7 seconds. After developing the photoresist in developer (AZ315MF, Clariant), the chrome layer was etched for 2 minutes in chrome etchant solution (Cyantek Co., Fremont, Calif.), and the photoresist removed by washing with acetone (Mallinckrodt Baker, Phillipsburgh, N.J.) and isopropanol (Mallinckrodt Baker). Following an additional cleaning in the plasma asher, a 3 μm layer of SU-8 2 (MicroChem) was spin-coated on the glass slide and processed according to the manufacturer's specifications. The resist was prebaked at 65° C. and then 95° C. for 1 minute each, and exposed to ultraviolet light through a mylar mask (CADArt, Poway, Calif.) aligned to the alignment marks in the chrome layer, followed by postbake (1 minute at 65° C. and 1 minute at 95° C.) and developing in Thinner P (Ashland, Marlborough, Mass.) for 1 minute (FIG. 4A1). The process was repeated using SU-8 photoresists with higher viscosities (SU-8 5 and SU-8 10) to produce the structures that were 5 and 20 μm tall on the same slide (FIG. 4A2-3). Good alignment of the structures was critical in producing quality molds; however, by designing the masks such that smaller structures were extended and partially overlapped by larger structures, small errors in alignment could be tolerated.

Thin Film Heaters. Glass coverslips covered with a thin film of chrome (50 Å) and gold (1000 Å, Goddard) were manufactured and processed similarly to the chrome covered slides, as described. After photoresist developing, the gold was etched for 20 seconds using a gold etchant solution (Cyantek), and then the chrome was etched for 40 seconds using a chrome etchant (FIG. 4B1). The photoresist was removed by washing with acetone and isopropanol, and the coverslips additionally cleaned in the plasma asher. A 15 μm layer of SU-8 10 was spin coated at 1500rpm, prebaked (3 minute at 65° C., 7 minutes at 95° C.), exposed to ultraviolet light (17 seconds at 15mW/cm$^2$) through a mylar mask, postbaked (1 minute at 65° C., 3 minutes at 95° C.) and developed (2 minutes, Thinner P) to form 100 μm diameter circular posts used as alignment structures for the elastomeric block on the heater elements (FIG. 4B2).

Figure 4:
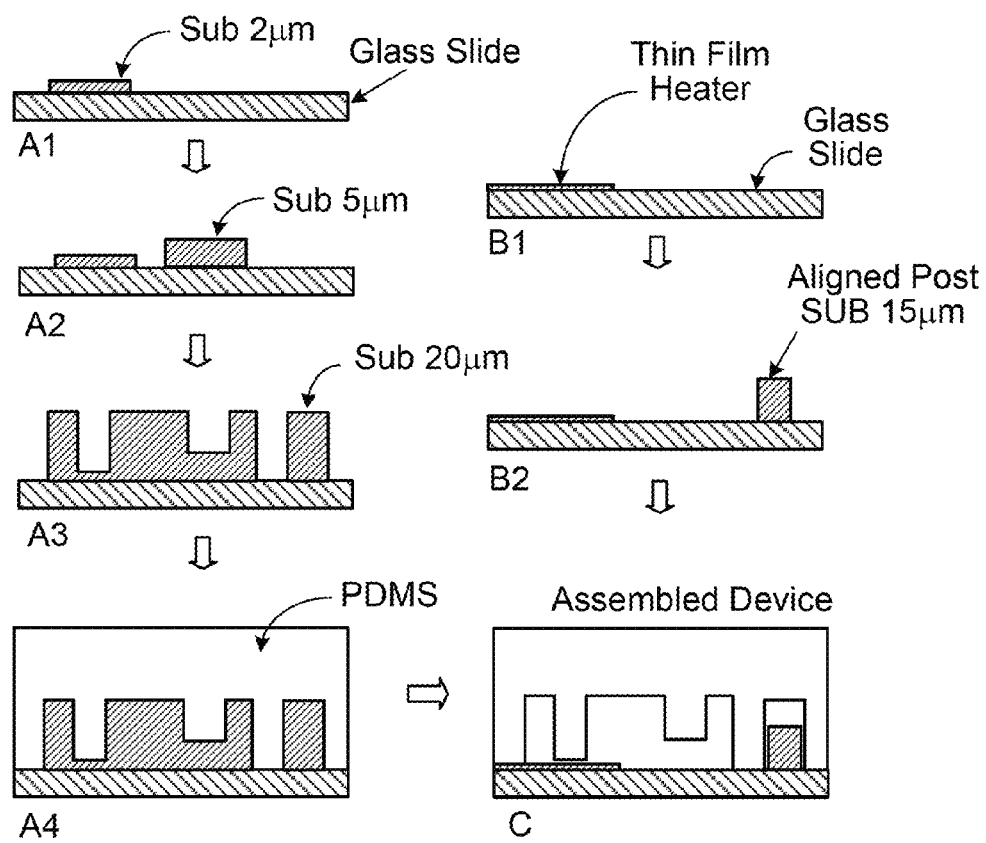
FIGS. 4A-4D are schematic diagrams of a device fabrication process. A. Three layers of different thicknesses of photopolymer were successively patterned on a glass slide (A1 to A3) and then used as a cast for PDMS (A4). B. On a different glass slide electrical heaters were etched in the gold thin film (B1) followed by the patterning of photopolymer alignment posts (B3). C. Corresponding wells in the PDMS mold were aligned with the posts on the heater slide, and the glass and PDMS were bound to form the final device. D. Scanning electron micrograph of the PDMS mold shows the upper and lower main channels, upper and lower lysis chambers, as well as the four air chambers.

Device Assembly and Surface Modification. Complementary structures were produced in Poly(dimethyl siloxane) (PDMS; Sylgard 184; Dow Corning, Midland, Mich.) by casting the polymer over the micropatterned mold (FIG. 4A4). For this purpose Sylgard 184 components A and B were mixed according to the manufacturer instructions (ratio 10:1 by weight), poured over the mold, degassed for 30 minutes under vacuum, and cured at 65° C. for at least 8 hours. After the incubation, the cured elastomer was peeled from the mold and through holes were punched using a sharpened 25-gauge needle, defining the inlets and outlets. The bonding surfaces of the PDMS and the heater coverslips were treated with oxygen plasma (25 seconds, 50W, 2% $O_2$) produced in the parallel plate plasma asher. Precise alignment between the PDMS and the coverslip was achieved under a stereomicroscope (Leica MZ8, Leica, Heerbrugg, Switzerland) using a lubrication layer formed by a 10 μL droplet of distilled water placed in between the two pieces. The alignment posts on the heater slide and the complementary channels in PDMS were helpful not only in the alignment process but also in stabilizing the assembly during further manipulation and heating of the device on a hot plate (5 minutes at 70° C.) for complete bonding (FIG. 4C).

The surface of the microchannels was subsequently modified to achieve supplementary hydrophobic characteristics. After bonding, the device was dehydrated on a hot plate at 120° C. for an additional 20 minutes. After the device cooled back to room temperature, a 5 mM solution of (Heptadecafluoro 1,1,2,2 tetrahydrodecyl) dimethyl-chlorosilane (Gelest, Morrisville, Pa.) in 99% toluene (Sigma-Aldrich, St. Louis, Mo.) was flushed through the device at a rate of 5 μL/min for 3 minutes, followed by a wash with 99% toluene for 2 minutes at the same rate. Nitrogen was passed through the channels, and the toluene absorbed into the PDMS during the previous steps was removed by heating the device to 120° C. on a hot plate for 8 hours.

Device Characterization. Contact angles between PBS, SDS and GTC and fluorosilane treated or untreated glass and PDMS were measured in static conditions. A drop of liquid (3μL) was gently placed on the surface of interest and observed through a microscope and images printed on paper (Sony video graphic printer UP860, Sony). The sample surface and the microscope were turned horizontal and leveled using a bubble-level indicator, and the sample and the objective were aligned such that the base of the droplet was on the microscope axis. Dynamic contact angles between PBS and fluorosilane treated PDMS were measured during the filling and clearing of water inside 50 μm wide channels of the device, and images were recorded and analyzed using Metamorph software.

The activation of the thermopneumatic actuator was characterized from serial photographs of the ejected air bubble and analyzed using Metamoph software. The distances were calibrated using a hemocytometer glass slide and the projected area of the air bubble measured for each time steps. The volumes were normalized to the volume of the air chamber.

Figure 5A:
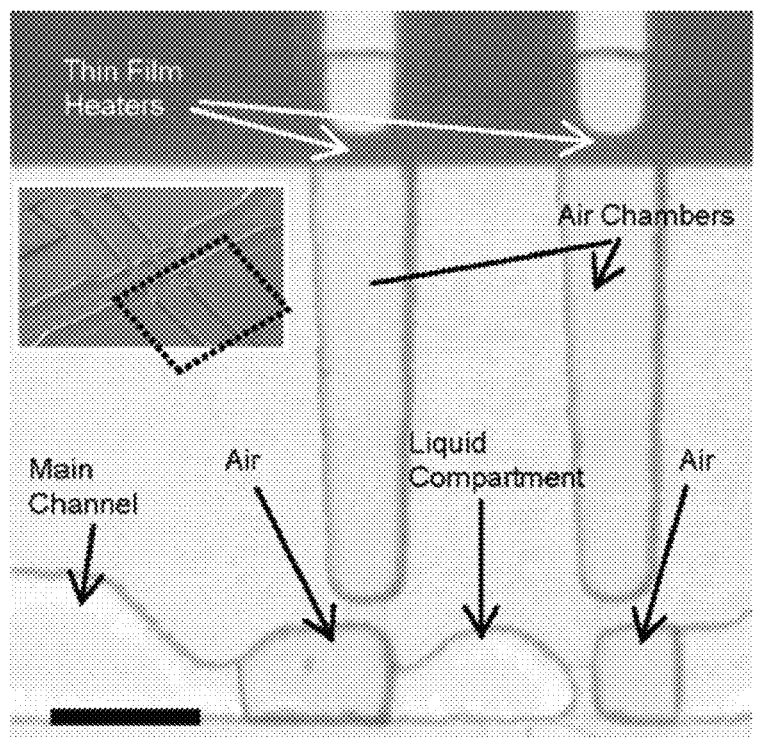
FIG. 5A is a micrograph of the functioning of the thermopneumatic actuator. Two air chambers, the corresponding thin film heaters and the main channel are shown using bright field microscopy. The inset outlines the location of the actuators on the device. The main channel was filled with phosphate buffered solution (PBS). Two air bubbles were formed by the expansion of the air in the air chambers after actuation, and a 25 pL volume of liquid was separated in the lysis chamber.
Figure 5B:
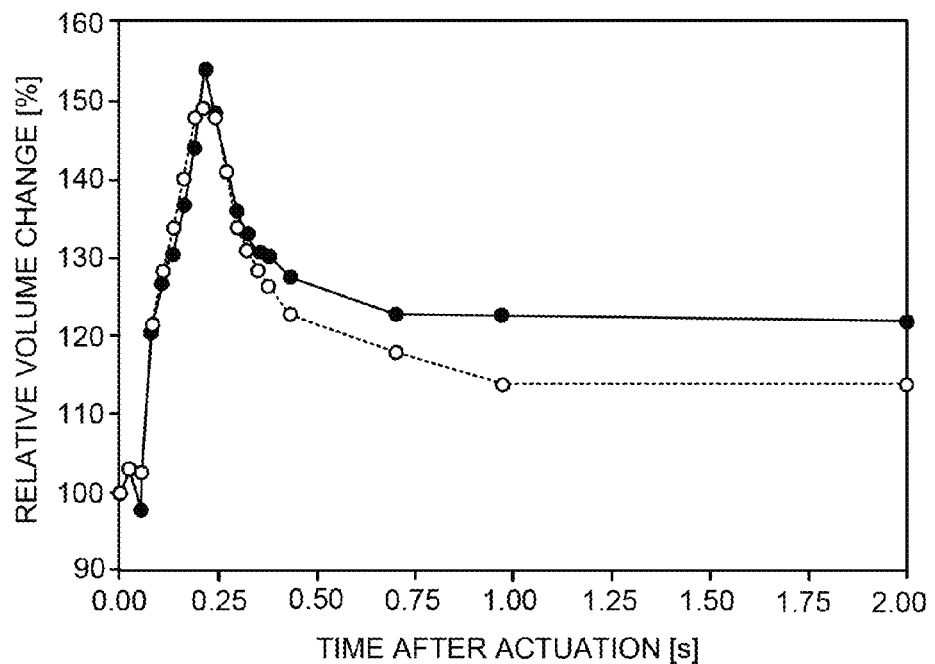
FIG. 5B is a graph of the change of the air volume from the chambers after actuation were calculated relative to the air chamber volume. One current pulse for 200ms determined the transitory expansion of the air form the chambers into the main channel. After actuation some air remained sequestered in the main channel, separating the liquid segments for at least 30 minutes. The volumes of the sequestered air bubbles on each side of the chambers were dependent on the geometry of the channel, and represented 20 and 14% from the air chamber volume, respectively.

The surface of the PDMS mold was sputter-coated with a 5 nm thick layer of gold-palladium and explored using a scanning electron microscope (JSM5600LV, Jeol Inc., Peabody, Mass.). Images were acquired using 5 kV acceleration voltage, and 160× and 500× magnification (FIGS. 5A-5B).

Cell Culture. Human lymphoblasts (MOLT-3, American Type Culture Collection, Rockville, Md.) were cultured in RPMI 1640 media (Gibco BRL Life Technologies, Rockville, Md.) supplemented with 10% fetal calf serum (Gibco) at 37° C. in an atmosphere of 10% $CO_2$. Cultured cells were split 1:10 and subcultured every 3 days. Before the experiment, 5 mL of a cell suspension was centrifuged, and the media removed. The pellet was resuspended in either phosphate buffered solution (PBS, Gibco), or a 6 μM solution of Cell-Tracker Orange CMTMR fluorescent dye (Molecular Probes, Eugene, Oreg.) in PBS, followed by 10 minutes incubation at 37° C. Cells were then centrifuged and washed once with PBS, and resuspended into 5mL of PBS. The final cell suspension was adjusted to a cell density of 10,000 cells/mL using PBS.

Lysing Solutions. Guanidine thiocyanate (GTC, Sigma), or sodium dodecylsulfate (SDS, Sigma) were dissolved in distilled water in order to prepare lysing solutions of 3M GTC, 0.2% SDS, or 0.1% SDS. For some of the experiments either Oregon Green Phalloidin or YOYO-1 iodide (Molecular Probes) were added to the 0.2% SDS, for a final concentration of 165 nM and 4 nM, respectively.

Separately, serial dilutions with concentrations of 6 μM, 600, 60 and 6 nM of the CMTMR fluorescent dye in PBS were prepared in 1 mL aliquots. Equal volumes (100 μL) of the dye and 3M GTC were passed through the chip and allowed to mix. Mixing of the lysing solutions with the cell suspension in the absence of the dye generated no signal above the background noise. Serial dilutions of 84, 42 and 21 nM Oregongreen phalloidin in 0.2% SDS were prepared and passed through the chip. Fluorescence intensity in the chambers was measured, and the background noise subtracted form measurements. An exponential curve was best fit to the data and preexponential and exponential coefficients were calculated for each of the two dyes.

Experimental Setup. Fluidic connections between the microfabricated device and 1 mL syringes containing the different solutions required for the experiments were made using 0.03" outer diameter Tygon® tubing (Small Parts, Miami Lakes, Fla.) and syringe needles (31 gauge) to fit tightly in the tubing. Electrical connections between the device and control electronics were made by soldering multifilament wires onto the gold pads at the periphery of the device. Four single pulse generators were fabricated in house, using two precision monostable circuits (74HC/HCT4538, Philips, Eindhoven, The Netherlands) and four power operational amplifiers (LM675, National Semiconductor, Santa Clara, Calif.) with the proper passive components. Single electrical pulses of 1 V and 100 mA, with the duration of 200 ms, were delivered to each heater, and synchronization of the pulses to the four heaters was obtained by controlling all four generators from a single foot switch. For the actual experiment, the device was mounted first on a glass slide (1×3 inches, Fisher) and then secured on the stage of an inverted microscope (Nikon Eclipse 2000) equipped with a color 8 bit digital video camera connected to a computer. Images were simultaneously recorded on the computer and on videotape (Sony SVO-9500MD). After the experiments, images were analyzed using MetaMorph software (Universal Imaging, Downingtown, Pa.). Video-recorded images were used to measure time intervals between events, using a manually controlled chronograph. The average of three separate measurements was usually calculated for each pair of events.

An isotonic phosphate buffer solution (PBS) was introduced through inlet A into the upper main channel (FIG. 4D), by the application of approximately 100N/m² pressure. After channel priming, a cell suspension containing an average number of 100 cells (100 μL of a 10,000 cells/mL cell suspension) was introduced through inlet B and driven slowly towards the upper lysis chamber. The capture of one cell in the cell chamber was achieved by the sieving effect at the cell capture dam, which stops cells sized larger than the depth of the channel (5a1m), while allowing the fluid to pass through. The capture of the cell was gentle because the flow rate of the fluid was low (approximately 100 μm/s). The flow in the upper main channel was stopped after the cell capture, and a lysing solution, was introduced in the lower main channel through inlet C. The cell was separated in a 25 pL volume of PBS, and simultaneously a 25 pL volume of the lysing solution was isolated in the lower lysing chamber, through the coordinated use of thermopneumatic actuators. When the air in the mixing channel was extracted by applying negative pressure through the sampling channel, the two liquids came into contact and mixing occurred by diffusion.

Cell lysis was observed either directly using phase contrast microscopy or indirectly, through the release of the fluorescent dye previously loaded inside the cells. Normal cells that appear as bright, shiny spheres in phase contrast microscopy, turn darker after the complete lysis of the membrane. The fluorescent dye starts leaking out of a cell immediately after membrane damage.

Results. A microfabricated device was developed and tested with the objectives of capturing one cell from a cell suspension, separating it in a closed volume, mixing with controlled volume of lysing solution, and making the cell lysate available for further analysis on or off the chip (FIG. 3). Two major challenges were simultaneously overcome to achieve quantitative analysis of intracellular contents, namely capturing and lysing one cell of interest inside a closed space and keeping the concentration of the intracellular components as close as possible to their original concentration. Although a number of devices for manipulating cells and small volumes of solutions have been described in the literature none of these could simultaneously overcome both challenges of sampling and mixing fluid volumes of comparable order of magnitude with cell volumes.

Device Design and Functioning. Our approach towards accomplishing the cell capturing and fluid mixing in closed volumes relied on the capillary effects in hydrophobic channels and the ability to manipulate small volumes of fluids through changes in the pressure at the liquid-gas interfaces. Whereas for the large majority of microfluidic devices the formation of air bubbles inside microchannels can render the device unusable, there are increasing numbers of examples of constructive uses of liquid-air interfaces for different applications. These include accurate metering of nanoliter volumes of liquids in microchannels wall-less control of the flow of liquid streams on hydrophobic surfaces and passive valves that would precisely stop the liquid flow at a certain position inside a channel without the need for any moving parts. In the device that we built, liquid gas interfaces were used both as passive valves to control the flow of fluid inside a network of connected microchannels, and also as barriers to completely isolate small volumes of liquids. The hydrophobic nature of the liquid-wall interaction was critical for stable and complete separation.

Passive valves were formed in our device by dimensional variations of to uniformly hydrophobic channels. According to the Young-Laplace equation (Eq. 1.), the pressure needed to move a liquid through rectangular microchannels formed between PDMS and glass is dependent on a, the surface tension of the liquid, w and h, the depth and the height of a channel, and θ the static contact angles between different liquids and the glass or PDMS surfaces:

$$P = \sigma \cos\theta_{PDMS}\left(\frac{2}{w} + \frac{1}{h}\right) + \sigma\cos\theta\text{glass}\left(\frac{1}{h}\right) \tag{1}$$

In the absence of surface modifications, the contact angles between liquids and the PDMS and glass walls of the device would have been relatively small and the capillary pressure positive, indicating capillary filling. Following fluorosilane treatment, contact angles between fluids and channel walls were measured in excess of 90°(Table 1), and calculated capillary pressure was negative, indicating a repellant force at the liquid gas interface. As a result, by adjusting the amount of pressure applied to the liquid we could control the entrance and the movement of liquids in channels of different sizes (Table 2). Thus, smaller channels can act as passive valves restricting the flow of fluids to the main channels during the device priming, and also trapping air inside the mixing channel and the chambers of the thermopneumatic actuator. In addition, air bubbles formed inside the main channels after thermopneumatic actuation, can effectively block the liquid flow through these channels. The relatively large differences in the pressure levels for different valves (Table 2) assured a robust control over the fluid movement inside the device. It also allowed for some flexibility in the composition of fluids introduced into the device, tolerating for example the use of low concentrations of detergents.

TABLE 1

Measured contact angles between different liquids and the glass
and PDMS surfaces, before and after surface modification.

|  | σ[N/m] | Contact Angle Glass | | Contact Angle PDMS | |
|---|---|---|---|---|---|
|  |  | Before fluoro-silane treatment | After fluoro-silane treatment | Before fluoro-silane treatment | After fluoro-silane treatment |
| PBS | $72.0 \times 10^{-3}$ | 15° | 87° | 100° | 99° |
| 3M GTC | $67.8 \times 10^{-3}$ | 5° | 85° | 93° | 100° |
| SDS 0.1% | $60.5 \times 10^{-3}$ | 10° | 78° | 92° | 97° |
| SDS 0.2% | $49.0 \times 10^{-3}$ | 5° | 70° | 66° | 90° |

TABLE 2

Calculated pressure differences required for driving
particular liquids in different microchannels of the
device after surface modification [$\times 10^3$ N/m$^2$].

| | Pressure Gradient [$\times 10^3$ N/m$^2$] | | | |
|---|---|---|---|---|
|  | Main Channel | Chamber Passive Valve | Mixing Channel | Air Chamber Passive Valve |
| PBS | −2.6 | −4.3 | −12.3 | −21.6 |
| 3M GTC | −1.6 | −2.7 | −7.7 | −13.5 |
| SDS 0.1% | −1.0 | −1.7 | −4.8 | −8.5 |
| SDS 0.2% | −0.3 | −0.6 | −1.7 | −3.0 |

The formation of picoliter volume compartments was achieved by the use of thermopneumatic actuators and by exploiting of the hysteresis in the contact angle of moving liquid-air interfaces. While other microfabricated devices for subnanoliter liquid volume separation previously reported the use of mechanical valves for isolation of volumes as small as 750 pL or the use of external sources of air flow for the separation of volumes of 600 pL, our approach allowed the formation of 25 pL fluid compartments.

One key feature for separating small volumes using our device was the simultaneous and symmetrical generation of small air bubbles at the ends of the chambers, through the coordinated action of four thermopneumatic actuators. These actuators used on-chip thin film elements to heat and pressurize the air initially trapped in the air chambers, circumventing the need for external sources of pressure. Upon heater actuation, the approximately 100 picoliter volume of air in each chamber almost doubles its volume, expanding it into the main channels and breaking the continuity of the liquid column (FIG. 5A). The pressure required for the initial outburst of air from the air chamber and through the 2×12.5 μm channel was estimated to $4.2 \times 10^4$ N/m$^2$, and observations of the bubble formation in the main channel suggested that this pressure was achieved within 50 milliseconds after the heaters were turned on. During the air expansion we measured a dynamic contact angle of 55-60° between a PBS solution and the walls of the channel, and advancing speeds of the interface up to 300 μm/s. The direction and magnitude of movement of the newly formed liquid-air interfaces were passively controlled through variations of the cross-sectional area of the main channels in the vicinity of the lysis chambers. Constrictions next to each of the lysis chambers prohibited the entrance of the air, while increasing cross sectional area of the channels away from the chambers directed the expansion of the air bubbles outwards. During bubble formation and expansion, the symmetry in speed and amplitude for the newly formed air liquid interfaces on both sides of the lysing chambers assured that the 25 pL fluid volumes were not evicted form the compartments where they were separated.

To achieve actuation, electricity was applied to the heaters for only 200 milliseconds, short enough to avoid major beating of the liquids in the channels. After the heaters were turned off, the air cooled down very fast, mainly through heat conduction through the thin glass slide. Consequently, the air retracted, and the contact angle for the moving interface increased to 105°. Because of the new pressure balance, the air did not return to its initial volume. Depending on the shape of the channel, between 14 and 20% of the initial air volume remained trapped inside the main channel (FIG. 5B). This residual volume could increase to 33% if two successive pulses at 200 milliseconds time interval were applied. These observations suggests that other mechanisms in addition to the hysteresis in contact angle may be responsible for reaching the new equilibrium state, e.g., the water evaporation at the liquid air interface and gas transport through the highly diffusive PDMS.

The formation of liquid compartments inside a channel has a number of advantages over other approaches to isolating cells into small volumes of fluid. Isolation of cells into droplets that have all or part of their surface exposed to atmospheric air is usually complicated by the liquid evaporation, that may happen in seconds for droplets of nanoliter size. When droplets are isolated in oil the use of detergents inside the droplet or diffusion of liposoluble components into the oil may become a problem. In our approach, most of these drawbacks were avoided by containing the droplet between solid walls and by using very small air volumes that become saturated with water vapors immediately after actuation.

Overall, passive and active controls in the microfluidic network allowed the sequential management of three main steps in the functioning of the device, namely main channels filling and cell capture, compartmentalization, and mixing followed by cell lysis (FIG. 3). Liquid mixing was controlled by the pressure applied from the exterior through the actuation channel. After the splitting of the two liquid columns, air was progressively extracted from the mixing channel using a syringe, forcing the contact between the two liquids (FIG. 3). The smaller cross sectional area of the junction between the sampling and the mixing channels prevented the liquids in the mixing channel form entering the sampling channel. The lysing solution had lower surface tension that the cell suspension solution, and thus upon actuation the lysing solution flowed into the mixing channel and the contact between the liquids in the two chambers occurred closer to the cell capture chamber. After the two liquids came into contact, mixing took place by diffusion. Additional mixing could be accomplished by repeatedly drawing and pushing back the liquid from the mixing channel into the sampling channel.

Figures 6A, 6B:
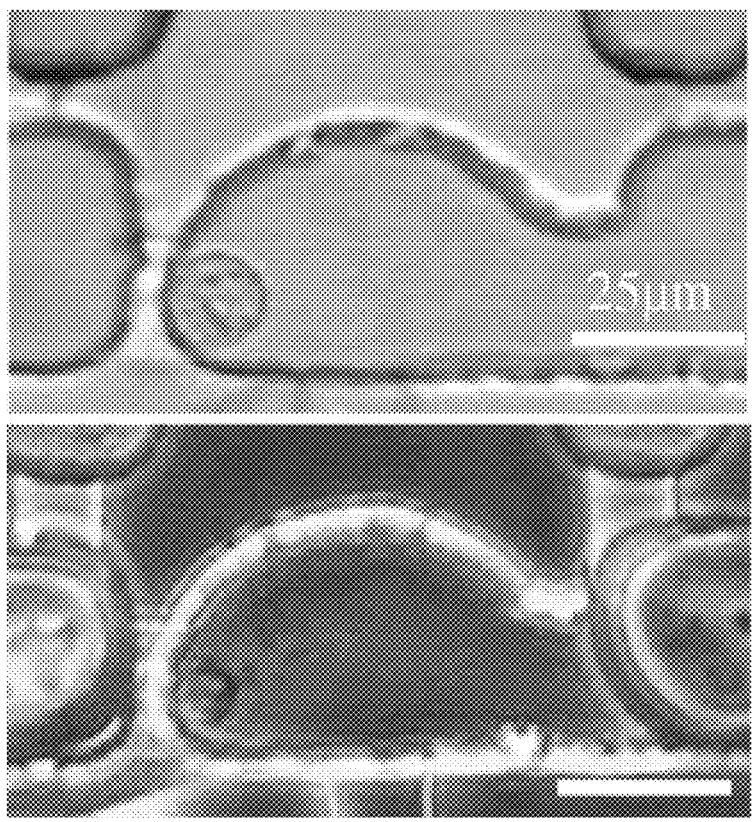
FIGS. 6A and 6B are micrographs of cell lysis. A. Bright filed microscopy image showing one MOLT-3 lymphoblast cell captured in the upper lysis chamber and isolated in 25 pL of PBS. B. Phase contrast of the upper lysis chamber showing the remaining structures following the chemical lysis of one cell using 0.2% SDS. Scale bar is 251 µm and is identical for the two images.

Single Cell Lysis and Biochemical Assays. Cells were lysed by the detergent action of the lysing agent on the cell membrane (FIG. 6). Both GTC and SDS have low molecular weight (118 and 288, respectively) and diffuse very fast in the compartments upon contact. Both act on the lipid component of the cell membranes, and GTC has additional denaturing action on the proteins. The time from the contact of the solutions in the two compartments until the lysis of the cell was determined from the microscopy images recorded on tape during experiments. Cell lysis in the presence of GTC occurred in 0.5 to 1 second after the contact of the compartments, while it was slower for SDS, 3 and 10 seconds for concentration of SDS was of 0.2% and 0.1%, respectively.

Following the lysis of the cell membrane, soluble components started diffusing out of the cell and into the device chambers and their initial intracellular concentration was estimated from their final concentration in the chambers. In one assay, cells were loaded with Cell-Tracker Orange CMTMR fluorescent dye, and the fluorescence intensity versus time following cell lysis was recorded at two difference locations in the chambers (FIG. 7). The actual concentration of the dye in the chambers was calculated based on a calibration experiment, where several dilutions of the dye were flushed through the device, and the fluorescence intensity measured. Some characteristics of the CMTMR dye were helpful in calculating the initial free intracellular concentration. The CMTMR fluorescent dye is trapped inside the cells after loading by binding to glutathione and other biomolecules inside the cell, does not require enzymatic cleavage for activation, and does not change its fluorescent properties upon intracellular binding. It is also believed that while part of the dye molecules are bound and immobilized to structural proteins, others can still move inside the cell and could be released from the cell by disrupting the cellular membrane. Thus, the intracellular concentration of the fluorescent dye not bound to structural proteins could be estimated from the free dye concentration inside the chambers following the cell lysis. Considering that the dye released in the chambers had been initially contained only inside the cell of approximately 1 pL volume, a volume that is 50 times smaller than the volume of the two chambers, the intracellular concentration of the fluorescent dye not bound to structural proteins was estimated at 2 µM (FIG. 7).

Apart from the microfabricated device, only standard imaging equipment was required for determining the dye concentrations inside the cell. Direct measurements with intact cells would have been difficult because of the spherical geometry of the cell and diffraction phenomena. In addition, such measurements would have provided the total dye concentration, with no distinction between the free and structurally bound dye molecules. If the cell would have been lysed in a "macro" vial, of 100 µL volume, the final concentration of the dye in the solution would have been 6 orders of magnitude lower, in the picomolar range ($2 \times 10^{12}$M), beyond the detection limit for regular digital cameras. The lysis of the same cell inside a microfabricated channel with flow, would have posed the problem of recording and analyzing a signal that was rapidly decaying over time. Moreover, because the dye release from the cell was in general not sudden, but a slow process developing over tens of seconds, it would have been difficult to infer from a single concentration versus time curve what the initial intracellular concentration of the molecule of interest had been.

Figure 8:
FIG. 8 is a fluorescence image of actin from one cell after lysis. One cell was lysed using a solution containing 0.2% SDS and simultaneously actin was stained by Oregon-Green phalloidin. The filamentous actin remains stable after cell lysis and staining for at least 30 minutes in the absence of any cell fixation steps. The equilibrium concentration of phalloidin in the chambers is used to evaluate the amount of filamentous actin inside the cell.

One important characteristic of the cell lysis in our microfabricated device was that the process was mechanically gentle on the cell, since the lysing agent reached the cell by diffusion in the absence of any significant convection. By using phase contrast microscopy we observed that following the contact of the cell with the lysis solution, the appearance of the cell changes dramatically, from normal smooth and shiny to rough and dark (FIG. 6). However, the size of the cellular image does not change significantly following the lysis for at least 20 minutes, and we believe that the insoluble cytoskeleton components and larger molecules maintain their initial position and configuration in the absence of considerable mechanical stress. Preliminary data, through fluorescent dye staining suggests that at least actin and DNA retain their position after cell lysis. When YOYO-1 dye was introduced in the lysis chamber with the lysing solution, it stained the DNA indicating its localization on the previous cell site. The presence of filamentous actin was confirmed by the use of Oregon-green phalloidin (FIG. 8).

In addition to localization, the intracellular concentration of filamentous actin was estimated using the microfabricated device. One cell was captured in the upper lysis chamber, and then exposed to a solution of detergent (2% SDS in water) and Oregon-green phalloidin (165nM). Following the lysis of the cell membrane, phalloidin dye molecules can enter the cell and bind to filamentous actin specifically and with high affinity, following a stoichiometric ratio of 1:1. An estimated number of $2.5 \times 10^6$ molecules were introduced in the two chambers, and after 30 seconds, when quasi-equilibrium was reached, some molecules were concentrated on the actin containing structures, while the rest were uniformly distributed in the solution. Upon binding to actin, the Oregon-green fluorescent molecules increase their yield, and thus a direct estimate of the amount of actin is quite a laborious task. A correlation curve between the fluorescent signal and dye concentrations in the chambers away from the cell site could be generated. We found that the concentration of the fluorescent dye in the solution at 30 seconds decreased to 47 nM, corresponding to $1.4 \times 106$ molecules total. By the conservation of the number of molecules in a closed compartment, the number of molecules bound to actin and thus the total amount of filamentous actin in one cell was evaluated to $1 \times 10^6$ molecules/cell. This value is of the same order of magnitude with other estimates reported in the literature for the average amounts of filamentous actin per cell, obtained from bulk assays.

Again, only standard imaging equipment was used to perform the measurements. In addition, the flatness of both the top and bottom walls of the chamber allowed for signal integration over a larger proportion of the chamber surface. The lysis of the cell membrane was gentle and in the absence of any shear stress on cellular structures, thus precluding the need for stabilization of the filaments using formaldehyde, as it is usually the case in bulk quantification assays. In addition, phalloidin, which is known to prevent the depolymerization of F-actin after binding, reached the inside of the cell in seconds after membrane lysis because of micron diffusion distances, thereby stabilizing the filaments.

In addition to the two assays for intracellular unbound dye and for insoluble actin, previously presented, a wide range of chemical and biochemical assays that involve mixing of two components can potentially be performed using the microfabricated device. Various protocols for sample preparation involving manipulation and mixing of cells and reagents, which are currently handled on the "macroscale," could be implemented on existing lab-on-a-chip and sensor devices. Nonetheless, the use of fluids in volumes comparable to cell volume leads to limited dilution of the molecules of interest, and favors quantitative detection by improving the signal to noise ratio. If a biochemical assay is designed such that the system reaches a steady state after mixing, it may allow for longer signal integration over time, potentially improving on the sensitivity of the analysis and the precision of the measurements. The device and technique described herein may be used in an integrated microsystem to explore signaling, metabolic, or secretory aspects of cellular functions.

EXAMPLE 4

Extraction of Fluid from a Picoliter Mixing Device

Figure 9:
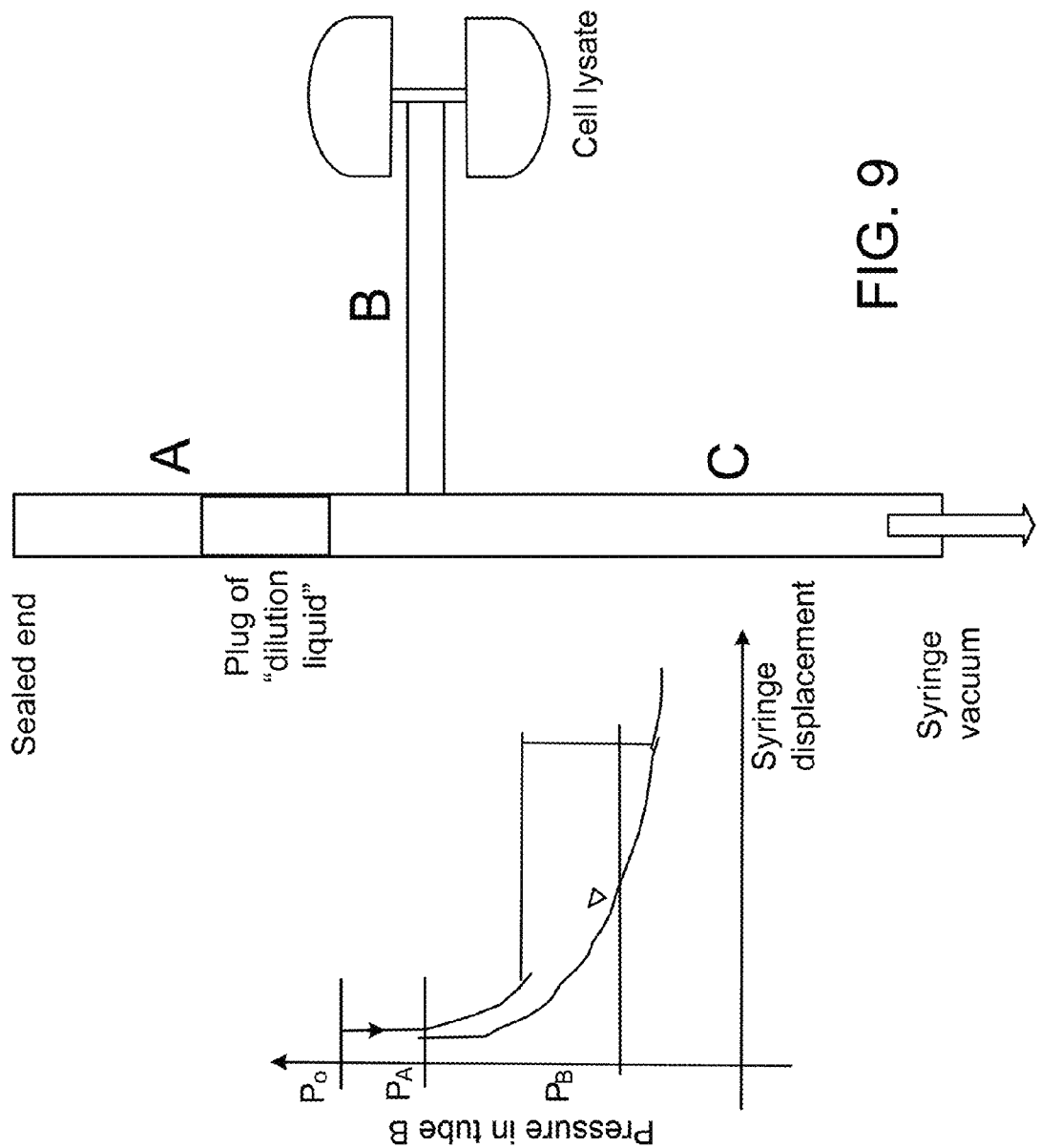
FIG. 9 is a schematic diagram of the removal of picoliter volumes of fluid from a device of the invention.
Figure 10:
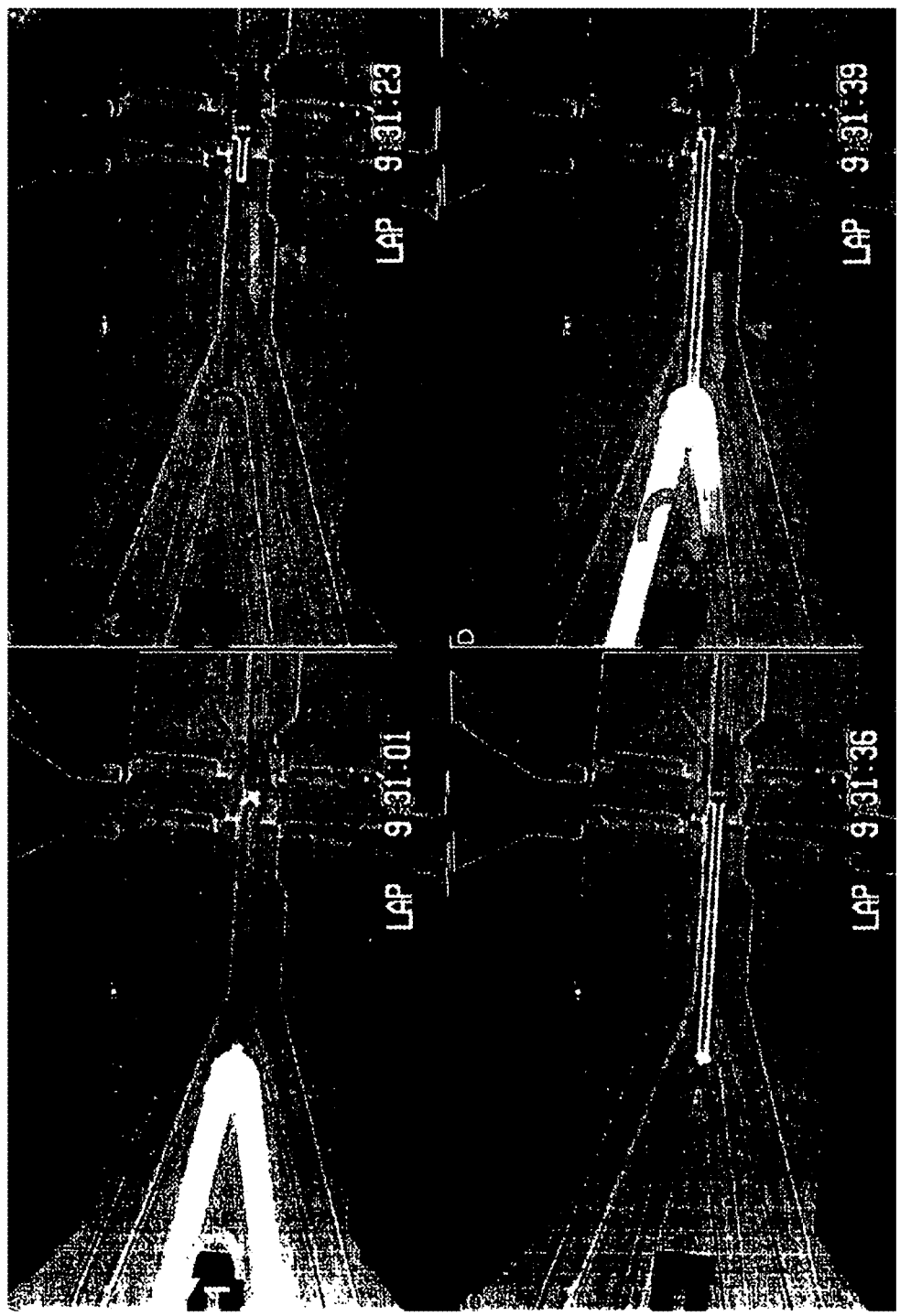
FIGS. 10A-10D are micrographs of the removal of picoliter volumes of fluid from a device of the invention.

FIGS. 9 and 10 illustrate a method for extracting the pL volume of fluid from the device after cell lysis. Page: 41 Referring to FIG. 9, the extraction capillary network is formed by capillary B connected to a larger hydrophobic capillary segments A and C. A plug of dilution liquid, of controlled volume (picoliter to microliter range), is introduced in the larger capillary, in section A and then the end is sealed, trapping a controlled volume of air between the liquid plug and the sealed end. A syringe is attached to the end of section C and used to decrease the pressure in the capillary network. Initially air in all sections is at atmospheric pressure $P_O$. Through syringe displacement the pressure in sections C and B is reduced, and when the threshold level $P_A$ is reached, the dilution liquid plug starts moving towards section C. At threshold level $P_B$ the cell lysate in section B starts moving towards section C. The volume of trapped air between the dilution plug and the sealed end can be calculated such that the position of the dilution plug at pressure PB is precisely at the confluence between sections A and B. Further decrease of pressure will pull both the dilution liquid and the cell lysate in section C. By opening the sealed end of section A, the final mixture can be extracted off the chip.

Page: 41

Referring to FIGS. 10A-10D, dilution liquid is introduced (arrow 1) in section A of the extraction capillary network. After sealing the upper end of section A pressure is reduced in the extraction capillary network, and the cell lysate is pulled inside section B (arrow 2). The dilution plug is also pulled towards section C. Cell lysate reaches the confluence of sections B and C before the dilution plug (FIG. 10C). The dilution plug (arrow 3) and cell lysate (arrow 4) are pulled together into section C of the extraction network.

EXAMPLE 5

Capture of Nucleic Acids Using the Continuous Flow Mixing Device

Figure 13:
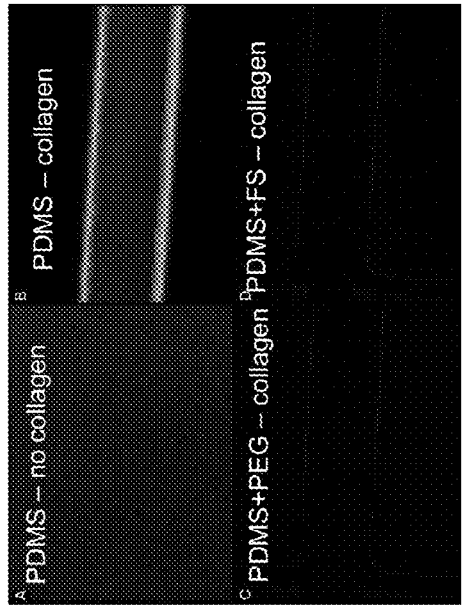
FIG. 13 is a schematic diagram of an assay for nucleic acids using a continuous flow mixing device.
Figure 13:
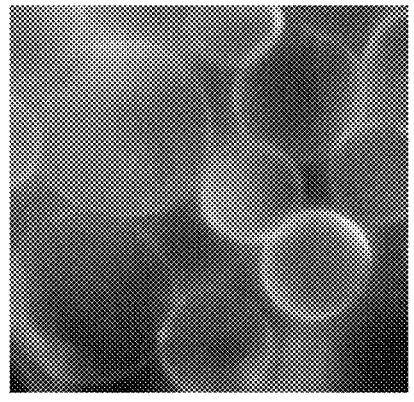

An assay employing the continuous flow mixing device is illustrated schematically in FIG. 13. A continuous flow mixing device is primed with ethanol, and sample is introduced through inlet 1. Cells and lysing solution are mixed in 1:2 ratio and allowed to interact for 30 seconds before being mixed with ethanol (1:1 ratio cell lysate to ethanol). The mixture is then passed over the silica gel particles and nucleic acids are captured (Landers Anal. Biochem. 2000, 283:175-191). Inlet 4 is opened and successively air, binding solution, and air are introduced at a 5 µL/min rate. The final step is the elution of nucleic acids from silica-gel particles by introducing water through inlet 4 and retrieving it at the outlet.

EXAMPLE 6

Isolation of RNA from Human B Lymphoblastoma Cells

Figure 14:
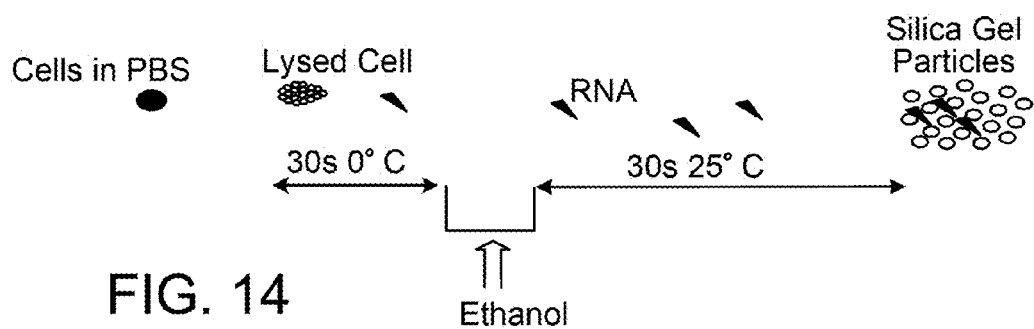
FIG. 14 is a schematic diagram of cell lysis and RNA capture on a continuous flow mixing device of the invention.

Isolation of RNA from samples containing less than 1000 cells has been explored in a continuous flow device as described herein. The device was designed to implement a common isolation protocol including the following steps: cell lysis using a chaotropic agent (Guanidinium thiocyanate—GTC), total RNA capture on silica gel particles, contaminant removal and RNA elution in distilled water. The device consists of a network of channels of different sizes connecting 3 inlets and one outlet (FIG. 14) and was manufactured using standard microfabrication technology, as outlined bellow.

Figure 15:
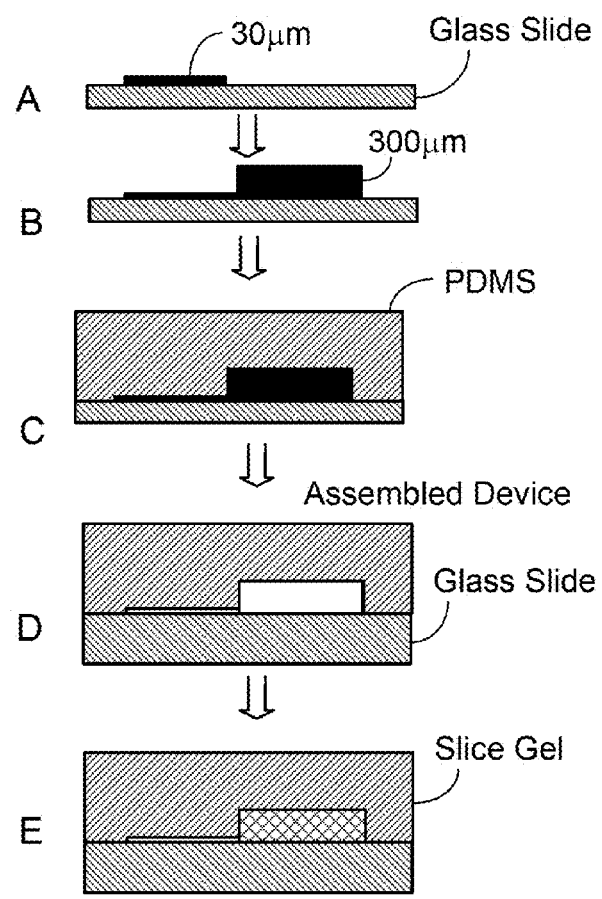
FIG. 15 is a schematic diagram for fabrication of a continuous flow mixing device of the invention
Figure 16:
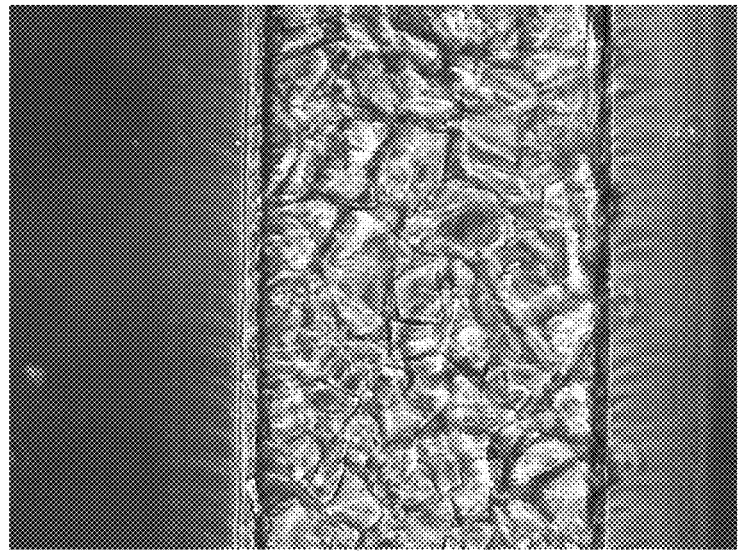
FIG. 16 is a micrograph of silica gel packed into a continuous flow mixing device of the invention. The channel is 1 mm wide.

The first fabrication steps were performed in a class 1000 clean room. Structures of 30 and 300 µm thicknesses were fabricated from SU8 epoxy based photoresist (MicroChem, Newton, Mass.) on glass slides (45×50×0.1mm, Fisher, Pittsburgh, Pa.) by exposure to ultraviolet light through a mylar mask (CADArt, Poway, Calif.). Then, channels complementary to these structures were produced in Poly(dimethyl siloxane) (PDMS; Sylgard 184; Dow Corning, Midland, Mich.) by casting the polymer over the micropatterned mold (FIG. 15). For this purpose Sylgard 184 components A and B were mixed according to the manufacturer's instructions (ratio 10:1 by weight), poured over the mold, degassed for 30 minutes under vacuum, and cured at 65° C. for at least 8 hours. After the incubation, the cured elastomer was peeled off from the mold and through holes were punched using a sharpened 25-gauge needle, defining the inlets and outlets. Complete channels were formed by bonding the PDMS cast on a glass microscope slide. Irreversible bonding was achieved by exposing the bonding surfaces to oxygen plasma (25 seconds, 50 W, 2% $O_2$) in a plasma asher, followed by contact and moderate pressure for 10 minutes. The surfaces of the channels were coated with (Heptadecafluoro 1,1,2,2 tetrahydrodecyl) dimethyl-chlorosilane (Gelest, Morrisville, PA) to prevent nucleic acid absorption. Silica gel particles (Sigma) were introduced in the larger channel through a temporary inlet that was permanently sealed afterwards (FIG. 16).

Samples containing 500 to 2000 human B lymphoblastoma cells (Raji cell line, ATCC, VA) in 10 µL phosphate buffered solution (PBS, Gibco, Rockville, Md.), 20 µL of 6M guanidinum thyocyanate (GTC, Sigma) and 30 µL ethanol (Sigma) ) were simultaneously loaded through the 3 separate inlets. Flow at a constant rate of 5 to 10 µL/min was achieved through suction at the outlet using a syringe pump. The size of the microchannels was chosen such that a 1:2 ratio between cell suspension and lysing solution and then a 1:1 ratio between the cell lysate and ethanol were achieved. The microfabricated device was transparent. Thus, it could be mounted on a microscope, and the precise number of cells entering the device and being lysed could be counted, as well as the mixing ratio between the different solutions. No pre or post treatment steps were necessary, nor were any centrifugation steps during the separation protocol. Following the cell lysis and RNA capture on the silica gel, the silica column was washed with washing buffer and then the captured nucleic acid eluted in 10 to 20 µL RNase free water (Ambion). The separation process can be performed in 10 to 20 minutes.

Figure 17:
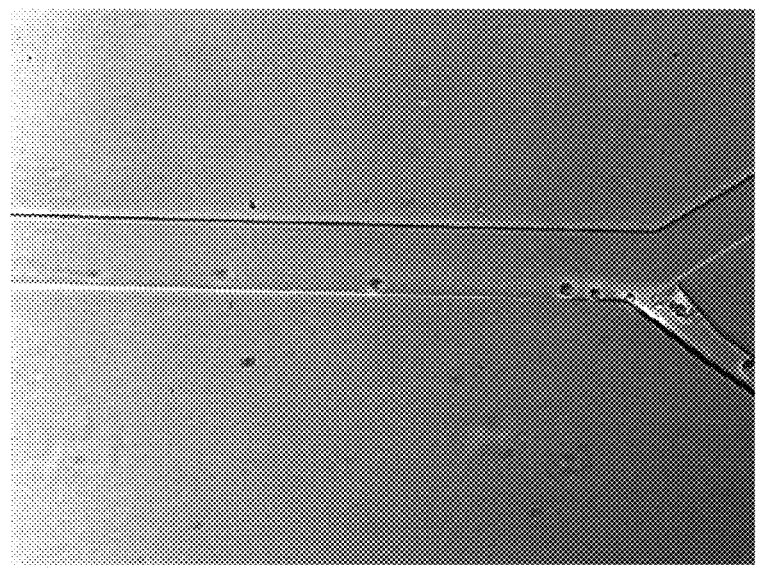
FIG. 17 is a micrograph of cell lysis in a continuous flow mixing device of the invention.

We used the microfabricated device described to isolate RNA from small samples containing a thousand cells or less. Human B lymphoblastoma cells from culture were centrifuged twice and resuspended in Ca free PBS, to a concentration of $10^5$ cells/ml. Samples of 10 µl cell suspension could be completely processed, and RNA extracted in approximately 20 minutes total with all steps involved in the separation being performed on the device. First, one stream of the cell suspension and one stream of the lysing solution were combined and allowed to mix by diffusion. As illustrated in FIG. 17, cells flowed from the reservoir into the device one by one, and lysis occurred in a fraction of a second, immediately after the confluence with the chaotropic lysing solution. Because of the continuous flow and mixing, the same conditions for cell lysis were present throughout the experiment, and every cell in the sample was lysed under the same conditions. Also, because of diffusion distances of the order of only tens of microns, concentrations of the chaotropic agent that are inhibitory of RNases were achieved in about a second after mixing and cell lysis. During the following steps, the cell lysate is mixed with ethanol and transported towards the silica gel column, then the separation column washed with the washing buffer, and the separation column washed with RNase free water to elute the RNA. Compared to standard techniques for RNA isolation, no centrifugation steps and only minimal liquid handling were required when using the microfabricated device.

Figure 18:
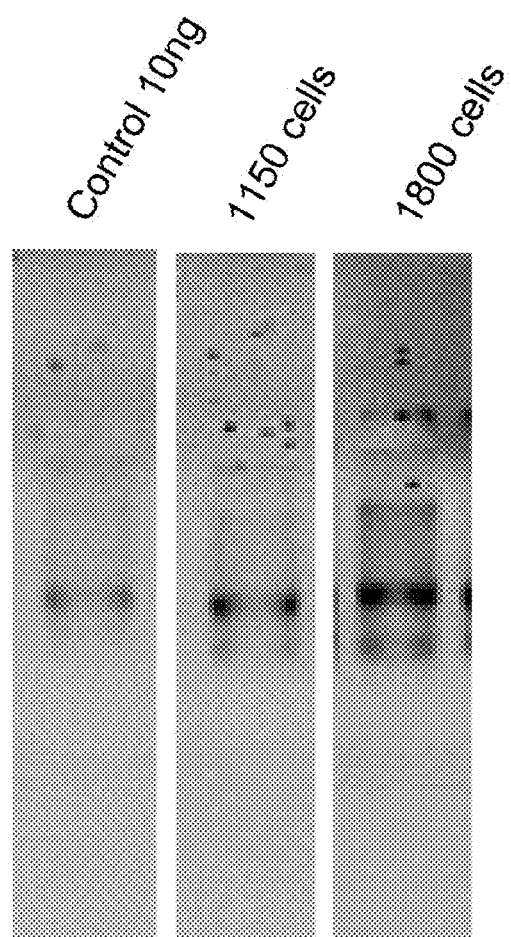
FIG. 18 is an RNA gel electropherogram showing tracks for 10 ng control, RNA isolated from 677 and 1200 B lymphoblastoma cells using a continuous flow mixing device of the invention.

Preliminary results show that it was possible to isolate good quality total RNA using a simple microfluidic device. Gel electrophoresis of 20 μL samples show that amounts of RNA of the order of nanograms could be extracted from cells (FIG. 18). The isolated RNA was of good quality and showed no signs of degradation, comparable to commercially available control RNA (Ambion). Significant amounts of DNA was also absent in the final sample.

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A device for contacting a first fluid and a second fluid, the device comprising:
    a first channel;
    a first fluid divider operable to isolate the first fluid in an isolated segment of the first channel from other first fluid in the first channel;
    a second channel;
    a second fluid divider operable to isolate the second fluid in an isolated segment of the second channel from other second fluid in the second channel; and
    a third channel connecting the isolated segment of the first channel and the isolated segment of the second channel, wherein the third channel is configured such that capillary pressure of an aqueous solution entering the third channel from the first channel or the second channel is negative.

2. The device of claim 1, wherein at least one of the first fluid divider or the second fluid divider comprises one or more sources for a fluid that is substantially immiscible with the first fluid and the second fluid.

3. The device of claim 2, wherein each of the one or more sources for the immiscible fluid is a substantially enclosed chamber fluidly connected to the first or second channel.

4. The device of claim 2, further comprising a constriction in the second channel sized to substantially prevent flow through the constriction of the fluid that is substantially immiscible with the first fluid and the second fluid.

5. The device of claim 1, further comprising a constriction in the first channel sized to prevent passage of particulate matter.

6. The device of claim 1, wherein the contact angle of an aqueous solution with a surface of the first channel is greater than 90°.

7. The device of claim 1, wherein the contact angle of an aqueous solution with a surface of the second channel is greater than 90°.

8. The device of claim 1, wherein the third channel is configured such that a contact angle of an aqueous solution with the third channel can be reduced to less than 90° by the application of light or an electric field to the third channel.

9. The device of claim 1, wherein the first or second channel comprises a chamber having a volume of 0.1 pL-100 μL.

10. The device of claim 9, further comprising:
    a chamber in the third channel, wherein the chamber in the third channel contains an affinity capture agent.

11. The device of claim 10, wherein said affinity capture agent comprises a bead, gel, or chemical species bound to a surface of the chamber in the third channel.

12. The device of claim 9, wherein the chamber has a volume of approximately 25 pL.

13. The device of claim 1, wherein the first channel comprises a first chamber having a volume of 0.1 pL-100 μL and the second channel comprises a second chamber having a volume of 0.1 pL-100 μL.

14. The device of claim 13, comprising:
    two first fluid dividers; and
    two second fluid dividers;
    wherein the two first fluid dividers are disposed flanking the first chamber and the two second fluid dividers are disposed flanking the second fluid chamber.

15. The device of claim 14, wherein
    each of the first fluid dividers comprises a substantially enclosed chamber fluidly connected to the first channel and a heat source operable to heat fluid in the substantially enclosed chamber fluidly connected to the first channel; and
    each of the second fluid dividers comprises a substantially enclosed chamber fluidly connected to the second channel and a heat source operable to heat fluid in the substantially enclosed chamber fluidly connected to the first channel.

16. The device of claim 14, wherein the two first fluid dividers and the two second fluid dividers are operable to simultaneously and symmetrically generate air bubbles at the ends of the first chamber of the first channel and at the ends of the second chamber of the second channel.

17. The device of claim 13, wherein the first chamber is partially defined by constrictions in the first channel and the second chamber is partially defined by constrictions in the second channel.

* * * * *

UNITED STATES PATENT AND TRADEMARK OFFICE
CERTIFICATE OF CORRECTION

| | |
|---|---|
| PATENT NO. | : 8,043,846 B2 |
| APPLICATION NO. | : 10/560661 |
| DATED | : October 25, 2011 |
| INVENTOR(S) | : Irimia et al. |

Page 1 of 1

It is certified that error appears in the above-identified patent and that said Letters Patent is hereby corrected as shown below:

Title page, Item [54], col. 1: Delete "FLUID" and insert --FLUIDS--.

Title page, insert Item --[56] Related U.S. Application Data Provisional Application No. 60/478,277, filed 06/13/2003--.

Col. 1, line 2: delete "FLUID" and insert --FLUIDS--.

Signed and Sealed this
Fifteenth Day of May, 2012

David J. Kappos
*Director of the United States Patent and Trademark Office*